United States Patent
Noteborn et al.

(10) Patent No.: US 6,238,669 B1
(45) Date of Patent: May 29, 2001

(54) PROTEINS ENCODED BY CHICKEN ANEMIA VIRUS DNA AND DIAGNOSTIC KITS AND VACCINES EMPLOYING SAID PROTEINS

(75) Inventors: Mathews H. M. Noteborn, Leiden; Gerden F. De Boer, Lelystad, both of (NL)

(73) Assignee: Leadd, bv (NL)

( * ) Notice: Subject to any disclaimer, the term of this patent is extended or adjusted under 35 U.S.C. 154(b) by 0 days.

(21) Appl. No.: 08/910,322

(22) Filed: Aug. 13, 1997

Related U.S. Application Data

(62) Division of application No. 08/484,939, filed on Jun. 7, 1995, now abandoned, and a continuation-in-part of application No. 08/030,335, filed as application No. PCT/NL91/00165 on Sep. 11, 1991.

(30) Foreign Application Priority Data

Sep. 12, 1990 (NL) .................................... 9002008

(51) Int. Cl.[7] .................................... A61K 39/12
(52) U.S. Cl. .................................... 424/186.1; 424/204.1; 530/350
(58) Field of Search .............................. 435/186.1, 204.1, 435/229.1, 5; 530/350; 536/23.72

(56) References Cited

U.S. PATENT DOCUMENTS 5,554,525 * 9/1996 Sondermeijer et al. .......... 435/240.1

FOREIGN PATENT DOCUMENTS

WO 90/02803   3/1990 (WO) .

OTHER PUBLICATIONS

Sambrook, J., et al., 1989a, "Expression of cloned genes in cultured mammalian cells", in *Molecular Cloning: A Laboratory Manual*, Cold Spring Harbor Laboratory Press, Cold Spring Harbor, New York, pp. 16.3–16.4.*

Sambrook, J., et al., 1989b, "Detection and analysis of proteins expressed from cloned genes", in *Molecular Cloning: A Laboratory Manual*, Cold Spring Harbor Laboratory Press, Cold Spring Harbor, New York, p. 18.2.*

Powell, M. F., et al., 1995, "Immunological and formulation design considerations for subunit vaccines", in *Vaccine Design: The Subunit and Adjuvant Approach*, Plenum Press, New York, pp. 2 and 27.*

Chiou et al., (1992) *Nuclei Acids Res.* 20: 1717–1723C2.

Chiou et al., (1994) *J. Virol.* 68:6553–6566.

Gelderblom et al. (1989) *Arch. Virol.* 109: 115–120.

Hanold et al. (1988) *J.Gen. Virol.* 69(6):1323–1329.

Innis & Gelfand, (1990) in: PCR Protocols: A Guide To Methods and Applications, Innis et al., Academic Press Inc., San Diego, CA pp. 3–20.

Jeurissen et al. (1992) *J. Virol.* 66:7383–7388.

McNulty et al. (1990) *Avian. Dis.* 34(2):352–358.

Noteborn et al., (1991) *J. Virol.* 65:313–3139.

Noteborn et al. (1992) *Avian Pathology* 21:170–118.

Noteborn et al. (1992) *Gene* 118:267–271.

Noteborn et al. (1992) in : Seminar organized for the European Commission from Dec. 15–16, 1992: New and Evolving Virus Diseases of Poultry, Eds., McNulty and McFerran, pp. 195–213.

Noteborn et al. (1993) in : *Vaccines 93*, Cold Spring Harbor Laboratory Press, pp. 299–304.

Ramakrishnan et al. (1993) *Nature* 362:219–223.

Rohde et al. (1990) *Virology* 176:648–651.

Ritchie et al. (1989) *Virology* 171:83–88.

Shi–Mei Zhuang et al. (1995) *Cancer Research* 55:486–489.

Than & Stanislawek, (1992) *3 Arch. Virol.* 127:245–255.

Todd et al. (1990) *Avian. Dis.* 34(2):359–363.

Todd et al. (1990) *J. General Virology* 71:819–823.

Todd et al. (1991) *Arch. Virol.* 117:129–135.

Woolston et al. (1988) *Plant Molecular Biology* 11:35–43.

Noteborn et al., 1991, "Characterization of Cloned Chicken Anemia Virus DNA that Contains all Elements for the Infectious Replication Cycle", J. Virol. 65(6):3131–3139.*

* cited by examiner

Primary Examiner—Laurie Scheiner
Assistant Examiner—Jeffrey S. Parkin
(74) *Attorney, Agent, or Firm*—Jennifer Wahlsten; Barbara Rae-Venter; Rae-Venter Law Group P.C.

(57) ABSTRACT

Circular double-stranded replication intermediates were identified in low-molecular-weight DNA of cells of the avian leukemia virus-induced lymphoblastoid cell line 1104-X-5 infected with chicken anemia virus (CAV). To characterize the genome of CAV, we cloned linearized CAV DNA into the vector pIC20H. Transfection of the circularized cloned insert into chicken cell lines caused a cytopathogenic effect, which was arrested when a chicken serum with neutralizing antibodies directed against CAV was added. The 2,319-bp cloned CAV DNA contained all the genetic information needed for the complete replication cycle of CAV. The CAV genome probably contains only one promoter region and only one poly(A) addition signal. Southern blot analysis using oligomers derived from the CAV DNA sequence showed that infected cells contained double- and single-stranded CAV DNAs, whereas purified virus contained only the minus strand. The CAV DNA sequence has three partially overlapping major reading frames coding for putative peptides of 51.6, 24.0, and 13.6 kDa. The claimed invention is directed toward immunogenic and vaccine compositions comprising these novel peptides.

13 Claims, 12 Drawing Sheets

```
         10         20         30         40         50         60         70         80         90        100
GAATTCCGAG TGGTTACTAT TCCATCACCA TTCTAGCCTG TACACAGAAA GTCAAGATGG ACGAATCGCT CGACTTCGCT CGCGATTCGT CGAAGGCCGG 110        120        130        140        150        160        170        180        190        200
GGGCCCGGAGG CCCCCCGGTC CCCCCCCTCC AACGAGTGA GCACGTACAG GGGCGTACGT CATCCGTACA GGGGGGTACG TCATCCGTAC AGGGGGGTAC 210        220        230        240        250        260        270        280        290        300
GTCACAAAGA CGCGTTCCCG TACAGGGGGG TACGTCACGC GTACAGGGGG GTACGTCACA CCCAATCAAA AGCTGCCACG TTGCGAAAGT GACGTTTCGA 310        320        330        340        350        360        370        380        390        400
AAATGGGCGG CGCAAGCCTC TCTATATATT GAGCGCACAT ACCGGTCGGC AGTAGGTATA CGCAAGGCGG TCCGGGTGA TGCACGGGAA CGGCGCACAA 410        420        430        440        450        460        470        480        490        500
CCGGCCGCTG GGGGCAGTGA ATCGGCGCTT AGCCGAGAGG GGCAACCTGG GCCCAGCGGA CCCGCGCAGG GGCAAGTAAT TTCAAAATGAA CGCTCTCCAA 510        520        530        540        550        560        570        580        590        600
GAAGATACTC CACCCGGACC ATCAACGGTG TTCAGGCCAC CAACAAGTTC ACGGCCGTTG GAAACCCCTC ACTGCAGAGA GATCCGGATT GGTATCGCTG 610        620        630        640        650        660        670        680        690        700
GAATTACAAT CACTCTATCG CTGTGTGGCT GCGCGAATGC TCGCGCTCCC ACGCTAAGAT CTGCAACTGC GGACAATTCA GAAAGCACTG GTTTCAAGAA 710        720        730        740        750        760        770        780        790        800
TGTGCCGGAC TTGAGGACCG ATCAACCCAA GCCTCCCCTG AAGAAGCGAT CCTGCCGACCC CTCCGAGTAC AGGGTAAGCG AGCTAAAAGA AAGCTTGATT 810        820        830        840        850        860        870        880        890        900
ACCACTACTC CCAGCCGACC CCGAACCGCA AAAAGGCGTA TAAGACTGTA AGATGGCAAG ACGAGCTCGC AGACCGAGAG GCCGATTTTA CTCCTTCAGA 910        920        930        940        950        960        970        980        990       1000
AGAGGACGGT GGCACCACCT CAAGGCGACTT CGACGAAGAT ATAAATTTCG ACATCGGAGG AGACAGCGGT ATCGTAGACG AGCTTTTAGG AAGCCCTTTC 1010       1020       1030       1040       1050       1060       1070       1080       1090       1100
ACAACCCCCG CCCCGGTACG TATAGTGTGA GGCTGCCGAA CCCCCAATCT ACTATCACTA TCCGCTTGCA AGGGGTCATC TTTCTCACGG AAGGACTCAT 1110       1120       1130       1140       1150       1160       1170       1180       1190       1200
TCTGCCTAAA AACAGCACAG CGGCGGGCTA TGCAGACCAC ATGTACGGGG CGAGAGTCGC CAAGATCTCT GTGAACCTGA AAGAGTTCCT GCTAGCCTCA
```

FIG. 1A

```
1210       1220       1230       1240       1250       1260       1270       1280       1290       1300
ATGAACCTGA CATACGTGAG CAAAATCGGA CGCCCCATCC CCGGTGAGTT GATTGCCCAC GGGTCTAAAT CACAACCCGC GGACAATTGG CCTAATTGCT 1310       1320       1330       1340       1350       1360       1370       1380       1390       1400
GGCTGCCGCT AGATAATAAC GTGCCCTCCG CTACACCATC GGCATGGTGG AGATGGGCCT TAATGATCAT GCAGCCCACG GACTCTTGCC GGTTCTTTAA 1410       1420       1430       1440       1450       1460       1470       1480       1490       1500
TCACCCAAAG CAGATGACCC TGCAAGACAT GGGTCCCATG TTTGGGGCCT GGCACCTGTT CCGACACATT GAAACCCGCT TTCAGCTCCT TGCCACTAAG 1510       1520       1530       1540       1550       1560       1570       1580       1590       1600
AATGAGGGAT CCTTCAGCCC CGTGGCGAGT CTTCTCTCCC AGGGAGAGTA CCTCACGCGT CGGGACGATG TTAAGTACAG CAGCGATCAC CAGAACCGGT 1610       1620       1630       1640       1650       1660       1670       1680       1690       1700
GGCAAAAAGG CGGACAACCG ATGACGGGGG GCATTGCTTA TGCGACCCGG AAAATCAGAC CCGACGACCA ACACTACCCT GCTATGCCCC CAGACCCCCC 1710       1720       1730       1740       1750       1760       1770       1780       1790       1800
GATCATCACC GCTACTACAG CGCAAGGCAC GCAAGTCCGC TGCATGAATA GCACGCAAGC TTGGTGGTCA TGGCACACAT ATATGAGCTT TGCAACACTC 1810       1820       1830       1840       1850       1860       1870       1880       1890       1900
ACAGCACTCG GTGCACAATG GTCTTTTCCT CCAGGGCAAC GTTCAGTTTC TAGACGGTCC TTCAACCACC ACAAGGCGAG AGGACCCGGG GACCCCAAGG 1910       1920       1930       1940       1950       1960       1970       1980       1990       2000
GCCAGAGATG GCACACGCTG GTGCCGCTCG GCACGGACAC CATCACCGAC AGCTACATGT CAGCACCCGC ATCAGAGCTG GACACTAATT TCTTTACGCT 2010       2020       2030       2040       2050       2060       2070       2080       2090       2100
TTACGTAGCG CAAGGCACAA ATAAGTCGCA ACAGTACAAG TTCGGCACAG CTACATACGC GCTAAAGGAG CCGGTAATGA AGAGCGATGC ATGGGCACTG 2110       2120       2130       2140       2150       2160       2170       2180       2190       2200
GTACGCGTCC AGTCGGTCTG GCAGCTGGGT AACAGGCAGA GGCCATACCC ATGGCACGTC AACTGGGCGA ACAGCACCAT CTACTGGGGG ACGCAGCCCT 2210       2220       2230       2240       2250       2260       2270       2280       2290       2300
CAAAAGGGGG GGGGGCTAAA GCCCCCCCCC CTTAAACCCC CCCCTGGGGG GGATTCCCCC CCAGACCCCC CCTTTATATA GCACTCAATA AAGGCAGAAA

2310
ATAGATTTAT CCCACTAC
```

```
      360                                           380                               400
ACCGGTCGGCAGTAGGTATACGCAAGGCGGGTCCGGTGGATGCACGGGAACGGGGGACAACCGGGCCGCTG
              CAV-1     --->

430                          450                                   470
GGGGCAGTGAATCGGGCGCTTAGCCCGAGAGGGCAACCTGGGCCCCAGCGCGGGAGCCCAGCGGGAGGGGCAAGTAAT
              CAV-3   --->

500                                520                             540
TTCAAATGAACGCTCTCCAAGAAGATACTCCACCCCGGACCATCAACGGTGTTCAGGCCCACCAACAAGTTC
                                               <--- CAV-2
```

FIG. 4

| Direct repeat (DR) | | CAV isolates (number) |
|---|---|---|
| 5'-CGTACAGGGGGGTACGTCATC-3' | | |
| 1a | | 2 |
| 1b | | 5 |
|       T | | 7 |
| 2 | CA | 12 |
| 3 | CG | 12 |
| 4 | CA | 11 |
| | TCA | 1 |
| 12-bp insert | | |
| 5'-AAGAGGCGTTCC-3' | | 5 |
|   G | | 2 |
|     A | | 3 |
|         A | | 2 |

```
GCAGTAGGTATACGCAAGGCGGTCCGGGTGGATGCACGGGAACGGCGGACAACCGG
------------------
     CAV-1 -->

CCGCTGGGGGCAGTGAATCGGCGCTTAGCCGAGAGGGGCAACCTGGGCCcggatcc gaattcatcgataagcttgatatcgggccCAGCGGAGCCGCGCAGGGGCAAGTAAT TTCAAATGAACGCTCTCCAAGAAGATACTCCACCGGACCATCAACGGTGTTCAG
                                  --------------------
                                         <-- CAV-2
```

FIG. 7

```
ATGGCAAG ACGAGCTCGC AGACCGAGAG GCCGATTTTA CTCCTTCAGA AGAGGACGGT
                                                900
GGCACCACCT CAAGGCGACTT CGACGAAGAT ATAAATTTCG ACATCGGAGG AGACAGCGGT
                                                960
ATCGTAGACG AGCTTTTAGG AAGGCCTTTC ACAACCCCCG CCCCGGTACG TATAGTGTGA
                                               1020
GGCTGCCGAA CCCCCAATCT ACTATGACTA TCCGCTTCCA AGGGGTCATC TTTCTCACGG
                                               1080
AAGGACTCAT TCTGCCTAAA AACAGCACAG CGGGGGGCTA TGCAGACCAC ATGTACGGGG
                                               1140
CGAGAGTCGC CAAGATCTCT GTGAACCTGA AAGAGTTCCT GCTAGCCTCA ATGAACCTGA
                                               1200
CATACGTGAG CAAAATCGGA GGCCCCATCG CCGGTGAGTT GATTGCGGAC GGGTCTAAAT
                                               1260
CACAAGCCGC GGACAATTGG CCTAATTGCT GGCTGCCGCT AGATAATAAC GTGCCCTCCG
                                               1320
CTACACCATC GGCATGGTGG AGATGGGCCT TAATGATGAT GCAGCCCACG GACTCTTGCC
                                               1380
GGTTCTTTAA TCACCCAAAG CAGATGACCC TGCAAGACAT GGGTCGCATG TTTGGGGCT
                                               1440
GGCACCTGTT CCGACACATT GAAACCCGCT TTCAGCTCCT TGCCACTAAG AATGAGGAT
                                               1500
CCTTCAGCCC CGTGGCGAGT CTTCTCTCCC AGGGAGAGTA CCTCACGCGT CGGGACGATG
                                               1560
```

Fig. 8A

```
TTAAGTACAG CAGGGATCAC CAGAACCGGT GGCAAAAAGG CGGACAACCG ATGACGGGGG
                                                              1620
                                                                     1680
GCATTGCTTA TGCGACCGGG AAAATGAGAC CCGACGAGCA ACAGTACCCT GCTATGCCCC
                                                              1740
CAGACCCCCC GATCATCACC GCTACTACAG CGCAAGGCAC GCAAGTCCGC TGCATGAATA
                                                              1800
GCACGCAAGC TTGGTGGTCA TGGGACACAT ATATGAGCTT TGCAACACTC ACAGCACTCG
                                                              1860
GTGCACAATG GTCTTTTCCT CCAGGGCAAC GTTCAGTTTC TAGACGGTCC TTCAACCACC
                                                              1920
ACAAGGCGAG AGGAGCCGGG GACCCCAAGG GCCAGAGATG GCACACGCTG GTGCCGCTCG
                                                              1980
GCACGGAGAC CATCACCGAC AGCTACATGT CAGCACCCGC ATCAGAGCTG GACACTAATT
                                                              2040
TCTTTACGCT TTACGTAGCG CAAGGCACAA ATAAGTCGCA ACAGTACAAG TTCGGCACAG
                                                              2100
CTACATACGC GCTAAAGGAG CCGGTAATGA AGAGCGGATG ATGGGCAGTG GTACGCGTCC
                                                              2160
AGTCGGGTCTG GCAGCTGGGT AACAGGCAGA GGCCATACCC ATGGGACGTC AACTGGGCGA

ACAGCACCAT GTACTGGGGG ACGCAGCCCT
```

| | | | | | |
|---|---|---|---|---|---|
| TGCACGGGAA | CGGCGGACAA | CCGGCCGCTG | GGGGCAGTGA | ATCGGCGCTT | AGCCGAGAGG |
| | | | 420 | | |
| GGCAACCTGG | GCCCAGCGGA | GCCGCGCAGG | GGCAAGTAAT | TTCAAATGAA | CGCTCTCCAA |
| | | | 480 | | |
| GAAGATACTC | CACCCGGACC | ATCAACGGTG | TTCAGGCCAC | CAACAAGTTC | ACGGCCGTTG |
| | | | 540 | | |
| GAAACCCCTC | ACTGCAGAGA | GATCCGGATT | GGTATCGCTG | GAATTACAAT | CACTCTATCG |
| | | | 600 | | |
| CTGTGTGGCT | GCGCGAATGC | TCGCGCTCCC | ACGCTAAGAT | CTGCAACTGC | GGACAATTCA |
| | | | 660 | | |
| GAAAGCACTG | GTTTCAAGAA | TGTGCCGGAC | TTGAGGACCG | ATCAACCCAA | GCCTCCCTCG |
| | | | 720 | | |
| AAGAAGCGAT | CCTGCGACCC | CTCCGAGTAC | AGGGTAAGCG | AGCTAAAAGA | AAGCTTGATT |
| | | | 780 | | |
| ACCACTACTC | CCAGCCGACC | CCGAACCGCA | AAAAGGCGTA | TAAGACTGTA | AGATGGCAAG |
| | | | 840 | | |
| ACGAGCTCGC | AGACCGAGAG | GCCGATTTTA | CTCCTTCAGA | AGAGGACGGT | GGCACCACCT |
| | | | 900 | | |
| CAAGCGACTT | CGACGAAGAT | ATAAATTTCG | ACATCGGAGG | AGACAGCGGT | ATCGTAGACG |
| | | | 960 | | |
| AGCTTTTAGG | AAGGCCTTTC | ACAACCCCCG | CCCCGGTACG | TATAGTGT | |
| | | | 1020 | | |

Fig. 9

ATGAA

CGCTCTCCAA GAAGATACTC CACCCGGACC ATCAACGGTG TTCAGGCCAC CAACAAGTTC
                                      540                  600
ACGGCCGTTG GAAACCCCTC ACTGCAGAGA GATCCGGATT GGTATCGCTG GAATTACAAT
                                                             660
CACTCTATCG CTGTGTGGCT GCGCGAATGC TCGCGCTCCC ACGCTAAGAT CTGCAACTGC
                                                             720
GGACAATTCA GAAAGCACTG GTTTCAAGAA TGTGCCGGAC TTGAGGACCG ATCAACCCAA
                                                             780
GCCTCCCTCG AAGAAGCGAT CCTGCGACCC CTCCGAGTAC AGGGTAAGCG AGCTAAAAGA
                                                             840
AAGCTTGATT ACCACTACTC CCAGCCGACC CCGAACCGCA AAAAGGCGTA TAAGACTGT

Fig. 10

PROTEINS ENCODED BY CHICKEN ANEMIA VIRUS DNA AND DIAGNOSTIC KITS AND VACCINES EMPLOYING SAID PROTEINS

CROSS-REFERENCE TO RELATED APPLICATIONS

This application is a Div of Ser. No. 08/484,939 filed Jun. 7, 1995, abnd. and a continuation-in-part of U.S. Ser. No. 08/030,335 filed Mar. 3, 1993 now U.S. Pat No. 5,491,073, which was a U.S. National Stage Application of PCT/NL91/00165, filed Sep. 11, 1991, which disclosure is incorporated herein by reference Other related applications include U.S. Ser. No. 08/480,020, filed Jun. 1995, U.S. Ser. No. 08/454, 121, filed Jun. 7, 1995, U.S. Ser. No. 08/482,161, filed Jun. 7, 1995, U.S. Ser. No. 08/485,001, filed Jun. 7, 1995, and U.S. Ser. No. 08/489,666, filed Jun. 7, 1995.

INTRODUCTION

1. Field of the invention

This invention is in the fields of genetic engineering (gene manipulation) by means of the recombinant DNA (and RNA) technology, diagnostics and immunization/vaccination. More in particular, the invention relates to the detection, cloning and sequence analysis of the Chicken Anemia Virus (CAV) DNA genome and applications thereby made possible.

2. Background of the invention

The CAV virus that has not been classified so far causes infectious anemia in chicken. The virus was first isolated in Japan in 1979 and was given its name because of the serious anemia caused by it in young chicks (Yuasa, et al., (1979) *Avian Diseases* 23:366–385). The other symptoms of CAV infection are the atrophy of the bone marrow and destruction of lymphocytes in the thymus. Lesions occur in the spleen and liver.

Day-old chicks are most susceptible. In these animals lethargy, anorexia and a passing anemia are observed from 4 to 7 days after inoculation with CAV and about half of the animals die between 2 and 3 weeks after infection. With increasing age the natural resistance also increases. Upon infection at the age of seven days the chicks only develop a passing anemia after infection, and upon infection of 14 days old animals no anemia follows.

Protection against CAV infection and CAV disease symptoms is highly based on humoral immunological defense mechanisms. Vielitz, (1989) *Poultry Science* 68:34–35 developed a practical, rather effective method of prevention by means of a "controlled exposure" with CAV-infected liver suspensions in laying hens, the offspring thus acquiring maternal immunity. In Germany this method of immunization is used in practice, but it does not seem to be quite risk-free.

Animal experiments conducted in isolated poultry houses with the Centraal Diergeneeskundig Instituut (CDI) at Lelystad have confirmed the protective value of maternal antibodies. Here the "controlled exposure" was carried out with CAV multiplied in tissue culture. The presence of maternal antibodies against CAV fully prevented the CAV replication upon infection of day-old chicks from thus vaccinated mother animals. The CAV symptoms did not occur either. This passive protection was also obtained in offspring of immunized laying hens and also after injection of specifically pathogen-free (SPF) chicks with yolk extracts of eggs of the same immunized laying hens. The passive protection with respect to CAV infection by means of administration of CAV antibodies lasted until the age of 4 weeks. Then the passive protection was found to be incomplete. These experiments showed that maternal antibodies produced by vaccination of mother animals will play an important preventive role in the practical situation.

It also has been demonstrated by way of experiment that in chicks that survive the CAV infection a transient depletion of a specific population of thymus lymphocytes occurs (Jeurissen et al., (1989) *Thymus* 14:115–123). The thymus atrophy is the possible cause of the immunodepression causing CAV, with the result that specific vaccinations are less effective, e.g. against Newcastle Disease. CAV has been isolated several times in flocks with increased losses owing to Marek's disease, Gumboro's disease (Infectious Bursal Disease Virus, IBDV; Yuasa et aL, (1980) *Avian Diseases* 24:202–209) and in animals with Blue Wing Disease in association with retroviruses (Engström, (1988) *Avian Pathology* 17:23–32; Engström et al., (1988) *Avian Pathology* 17:33–50). With experimental double infections the enhancing properties of CAV with respect to other chicken viruses (e.g. Marek's Disease Virus, MDV, De Boer et aL, (1989) *Proceedings of the Thirty-Eighth Western Poultry Disease Conference*, Tempe, Ariz., p. 28) have been demonstrated. Recently a sharply increased inoculation reaction was observed in our own experiments after aerosol vaccination with Newcastle Disease vaccine and simultaneous CAV infection. CAV therefore leads to immunosuppressive and enhancing effects on other virus infections. These properties of CAV probably cause an increased incidence of virulent disease outbreaks in practice.

CAV seems to be spread all over the world. A considerable time after the CAV research had started in Japan the first CAV isolations were conducted in Europe, namely in Germany by Von Bülow ((1983) *Zentralbatt für Veterinarmedizin* B 30:742–750) and later by McNulty et al., ((1990) *Avian Pathology* 19:67–73) in the United Kingdom. In the Netherlands, the first isolations of CAV from material from the USA, Israel and Tunesia were conducted by De Boer et al., ((1988) *Proceedings First International Poultry and Poultry Diseases Symposium*, Manisa, Turkey pp. 38–48). The available literature data indicate that the isolates belong to one serotype but several field isolates are to be tested for their mutual relationship and possible differences in pathogenicity (McNulty et al., (1990) *Avian Pathology* supra). The spread of CAV within a flock probably occurs by infection via feces and air. Vertical transmission of virus to the offspring, however, also plays an important role in CAV epidemiology. In various countries the presence of CAV was demonstrated serologically.

Under tissue culture conditions CAV is hard to multiply. CAV hitherto causes only a cytopathologic effect (CPE) in MDV transformed lymphoblastoid cell lines from lymphomas of Marek's disease (MDCC-MSB1 cells) or Avian Leukaemia Virus (ALV) transformed lymphoblastoid cell lines from lymphoid leukosis (1104-X5 cells; Yuasa, (1983) *National Institute of Animal Health Quarterly* 23:13–20).

Relevant Literature

A recent study (by Todd et al., (1990) *J. General Virology* 71:819–823) describes virus particles (in purified CAV material) having a diameter of 23.5 nm which concentrate at a density of 1.33–1.34 g/ml in a CsCl gradient. The virus has one predominant polypeptide (Mr: 50,000) and a circular single-stranded DNA genome having a length of 2.3 kilobases. Two small viruses, the Porcine Circovirus and a virus associated with Psittacine Beak and Feather Disease, resemble CAV as regards the circular single-stranded DNA but have a smaller genome and a smaller virus particle diameter (Ritchie et al., (1989) *Virology* 171:83–88); (Tischer, et al., (1982) *Nature* 295:64–66). It was accepted for a long time that CAV belonged to the parvoviruses. Although most of the parvoviruses are single-stranded DNA viruses, they possess linear DNA, a larger genome and probably also another composition of viral polypeptides.

SUMMARY

It is generally accepted that cellular components involved in the replication and transcription of a virus are only functional if the DNA has a double-stranded form. A virus having a circular single-stranded DNA may occur in the cell in a phase in which it consists of double-stranded DNA. The present inventors have made use of this fact.

The present inventors have characterized the double-stranded CAV DNA having a length of 2.3 kilobase pairs in CAV-infected 1104-X5 and MDCC-MSB1 cells and cloned it in pIC-20H. The DNA was fully sequenced (see FIG. 1) (SEQ ID NO. 1). In a diagnostic test by means of labelled cloned CAV-DNA, CAV nucleic acids could be demonstrated in virus, liver and tissue culture preparations. Cloned CAV was found to have all the biological and pathogenic properties of wild type CAV, both in tissue culture and in animal tests.

PCR and hybridization experiments showed that the cloned complete CAV genome is representative of CAV in the field. By means of Southern analyses with $^{32}$P-labelled DNA probes it was demonstrated that all field isolates contained DNA molecules of 2.3 kb. Restriction enzyme analyses show that the cloned CAY DNA corresponds with the DNA of field isolates. In a dot blot assay it was demonstrated that with digoxigenin labelled cloned CAV DNA specifically hybridizes with DNA of the different field isolates. In PCR experiments using oligonucleotides the sequence of which was derived from the cloned CAV sequence (FIG. 4) (SEQ ID NO. 2), CAV-DNA was specifically amplified or recognized.

BRIEF DESCRIPTION OF THE DRAWINGS

FIG. 1 (SEQ ID NO. 1) shows the nucleotide sequence of the cloned CAV DNA. The total length is 2319 bases, the first G of the EcoRI site being taken as No. 1. The sequence of the DNA strand containing most of the largest open reading frames is shown in FIG. 1 and is called (+) strand.

FIG. 2 shows the predicted open reading frames (ORFs) of the cloned CAV DNA having a length of more than 300 bases for both DNA strands. The ORFs predicted for the three different start codons ATG, and GTG are shown in the tree subfigures 2A, 2B and 2C, respectively.

FIG. 3 (SEQ ID NO. 3–5) shows some predicted hairpin structures of the CAV genome consisting of single-stranded DNA. Between positions 55 and 135 (SEQ ID NO. 4–5) and between positions 2180 and 2270 (SEQ ID NO. 3) of the plus DNA strand very large hairpin structures are present in the (single-stranded) DNA form of CAV.

FIG. 4 (SEQ ID NOS: 23–25) shows the oligonucleotides used in the PCR. The DNA sequence and position of the oligonucleotides on the CAV genome are shown. The position of the nucleotides in the CAY genome corresponds with that shown in FIG. 1 (SEQ ID NO. 1).

FIG. 6 shows the sequences of the direct-repeat units and the 12-bp insert of the analyzed CAV isolates. Per specific sequence the number of the CAV isolates with this sequence is given.

FIG. 7 (SEQ ID NO: 22) shows the CAV-DNA sequences given from positions 349–535. Within the ApaI site the newly introduced 36-bp insert of pCAV/Apa. The CAV sequences are printed in upper and the sequences of the insert in lower case letters. The location of the amplication primers CAV-1 (SEQ ID NO: 23) and CAV-2 (SEQ ID NO: 25) are underlined. The arrows indicate their 5'–3' orientation.

DETAILED DESCRIPTION OF THE INVENTION

Figure 2A:
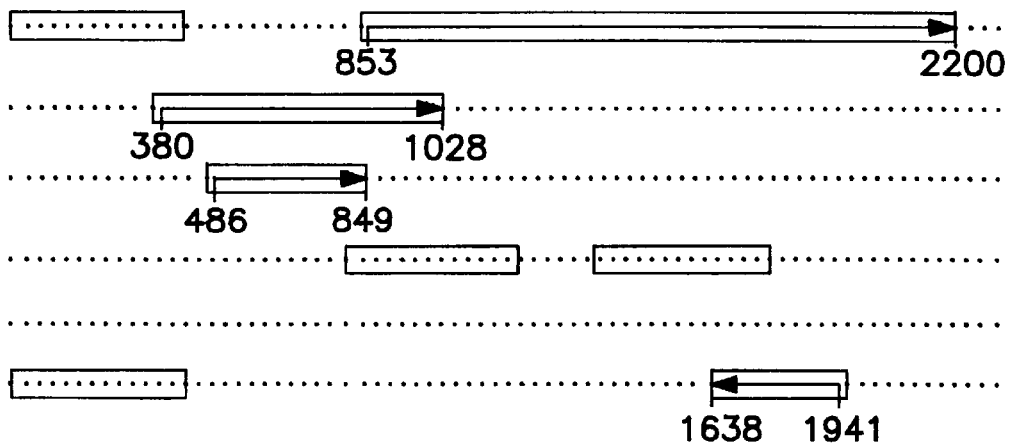
FIG. 2A shows the open reading frames beginning with the codon ATG.

The present invention provides in a first aspect recombinant genetic information in the form of labelled or unlabelled DNA or RNA, comprising a Chicken Anemia Virus (CAV) specific nucleotide sequence corresponding with or complementary to the nucleotide sequence of a CAV genome or part thereof. A preferred embodiment of the present invention consists of such recombinant genetic information comprising a CAV-specific nucleotide sequence corresponding with or complementary to the nucleotide sequence shown in FIG. 1 (SEQ ID NO. 1), a nucleotide sequence homologous thereto to at least 60%, or part thereof. This aspect of the invention consists of a nucleic acid selected from DNA and RNA, in any possible manifestation, i.e. both in the form of naked DNA or RNA and in the form of DNA or RNA packed in any way (i.e. in proteins or in virus particles) or connected with other matter (e.g., with a carrier or with a material functioning as a marker). The DNA may be both single-stranded and double-stranded DNA and may be both in linear and in circular form.

Characteristic of recombinant genetic information according to the invention is the presence therein of a CAV-specific nucleotide sequence. This CAV-specific sequence need not cover the entire genome of CAV and, from a practical point of view, only a specific part will be necessary and desirable for most of the applications.

A first preferred possibility is a CAV-specific nucleotide sequence corresponding with or complementary to a nucleotide sequence coding for a CAV protein and occurring in a CAV genome, or part thereof. Recombinant DNA comprising such a coding sequence may be used, e.g., for detecting CAV messenger RNA in a sample or may be used, e.g., within the scope of a process for producing CAV proteins or parts thereof. The words "part thereof" in principle comprise every part that can still be designated as CAV-specific. On a protein level this will be an epitope for most of the applications, i.e. an antigenic determinant recognizable by antibodies. Another possibility is that the recombinant genetic information according to the invention comprises a CAV-specific nucleotide sequence corresponding with or complementary to a nucleotide sequence having a regulatory function, occurring in a CAV genome, or part thereof. One example is the use of CAV promoter/enhancer elements in combination with sequences coding for a protein other than CAV protein, e.g., to enable expression of such non-CAV proteins in poultry (such as chickens) and other animals in which the regulatory signals of CAV are effective.

Both in the above case and in general the recombinant genetic information according to the invention may also comprise a nucleotide sequence not derived from a CAV genome. This "nucleotide sequence not derived from a CAV genome" may be formed by, e.g., a nucleotide sequence derived from a prokaryotic or eukaryotic expression vector. Thus, the invention comprises the possibility of an insertion of a CAV-specific sequence into a (viral or non-viral) vector suitable for expression in eukaryotic organisms or into a plasmid suitable for expression in bacteria. Furthermore, it is also possible that as "nucleotide sequence not derived from a CAV genome" recombinant genetic information according to the invention comprises a nucleotide sequence, not occurring in the CAV genome, having a regulatory function. The "nucleotide sequence not derived from a CAV genome", however, may also consist of a nucleotide sequence coding for (part of) a protein other than a CAV protein, e.g., if CAV regulation signals are used to express such a non-CAV protein (or part thereof) in a host accessible to the CAV virus, or if the recombinant DNA is to be used to produce a hybrid or fusion protein in which a CAV protein functions as a carrier for an epitope of a non-CAV protein or, conversely, a non-CAV protein functions as a carrier for an epitope of a CAV protein.

If the recombinant genetic information according to the invention is to be used within the scope of processes for detecting complementary DNA or RNA in a sample, the presence of a label may be necessary. A label as used herein is a marker suitable for use with DNA or RNA which enables or facilitates detection of the labelled DNA or RNA. A person skilled in the art knows many types of markers suitable for this purpose, such as radioisotopes (e.g., $^{32}$P), enzyme molecules (e.g., peroxidases), haptens (e.g., biotin), fluorescent substances, dyes, pigments (e.g., inorganic phosphors), and particulate markers (e.g., gold or selenium particles).

In a second aspect the invention relates to the use of recombinant genetic information as defined above, in particular for diagnostic purposes, immunization or vaccination purposes, or for the production of CAV or non-CAV proteins. More particularly, it concerns, e.g., a use of recombinant genetic information according to the invention as a CAV-specific probe or primer in a process for detecting CAV-DNA or -RNA, e.g. in a process of DNA/RNA slot blotting, Southern blotting, Northern blotting, in situ hybridization, DNA amplification by means of PCR, S1 mapping and primer extension, the invention also extending to a diagnostic kit for detecting CAV-DNA or -RNA in a process such as DNA/RNA slot blotting, Southern blotting, Northern blotting, in situ hybridization, DNA amplification by means of PCR, S1 mapping or primer extension, which diagnostic kit contains recombinant genetic information according to the invention as a CAV-specific probe or primer.

Further concerned is a use of recombinant genetic information according to the invention as a living virus vaccine to realize protection against CAV or another pathogen, the invention also extending to a vaccine preparation for immunizing against CAV or another pathogen, which preparation comprises recombinant genetic information according to the invention and optionally one or more carriers and adjuvants suitable for living virus vaccines.

Also concerned is a use of recombinant genetic information according to the invention as a cloning vector, i.e. a use of CAV-DNA as a kind of "eukaryotic plasmid" for avian systems in which gene fragments are incorporated into the complete or nearly complete CAV genome.

The use of recombinant genetic information according to the invention in a process for producing a CAV protein, part thereof or a protein other than a CAV protein, by in vitro or in vivo translation, is also included. The same applies to a prokaryotic or eukaryotic cell containing recombinant genetic information as defined above and, in particular, such a prokaryotic or eukaryotic cell capable of expression of at least one protein or protein part encoded by recombinant genetic information according to the invention. These different possibilities will be extensively explained below.

A following aspect of the invention is concerned with CAV protein or part thereof obtained by in vitro translation of recombinant genetic information according to the invention, comprising a nucleotide sequence coding for the CAV protein or part thereof, as well as CAV protein or part thereof obtained by isolation from a prokaryotic or eukaryotic cell containing recombinant genetic information according to the invention comprising a nucleotide sequence coding for the CAV protein or part thereof and capable of expression thereof. Also on the protein level the invention extends to the different applications, in particular the use of a CAV protein or protein part according to the invention for diagnostic purposes, immunization or vaccination purposes, or for the production of CAV-specific antibodies. For example, the invention includes the use of a CAV protein or protein part as defined above as a reagent for binding CAV-specific antibodies in an immunoassay process for detecting CAV-specific antibodies, e.g., an immunoperoxidase staining, an ELISA or an immunofluorescence assay, and a corresponding diagnostic kit for detecting CAV-specific antibodies in an immunoassay process such as an immunoperoxidase staining, an ELISA or an immunofluorescence assay, which diagnostic kit contains a CAV protein or protein part according to the invention as a reagent which binds CAV-specific antibodies.

The invention also comprises the use of a CAV protein or protein part as defined above as a subunit vaccine to provide protection against CAV, as well as a vaccine preparation against CAV, which preparation comprises a CAV protein or protein part according to the invention and optionally one or more carriers and adjuvants suitable for subunit vaccines. The use of a CAV protein or protein part as defined above in a process for producing CAV-specific polyclonal or monoclonal antibodies also falls within the scope of the invention.

In a further aspect the invention also relates to CAV-specific antibodies produced by means of a CAV protein or protein part as defined above, as well as the different uses for such CAV-specific antibodies, e.g. for diagnostic purposes, immunization or vaccination purposes, or for preparative purposes. For example, it concerns a use of CAV-specific antibodies according to the invention as a CAV protein binding reagent in an immunoassay process for detecting CAV protein, as well as a diagnostic kit for detecting CAV protein in an immunoassay process, which diagnostic kit contains CAV-specific antibodies according to the invention as CAV protein binding reagents.

A further example is a use of CAV-specific antibodies according to the invention for passive immunization against CAV infection, as well as an immunization preparation for passive immunization against CAV, which preparation includes CAV-specific antibodies according to the invention and optionally one or more carriers and adjuvants suitable for passive immunization preparations. Specifically concerned is immunization of laying hens with recombinant products according to the invention.

As regards preparative applications, one example is the use of CAV-specific antibodies according to the invention in a process for isolating and/or purifying CAV protein. The most important uses will be explained more extensively in the following detailed description of the invention.

EXAMPLES

Depositing the CAV Clone pIC-20H/CAV-EcoRI

A glycerol stock of HB101 cells transformed with the plasmid pIC-20H/CAV-EcoRI was deposited with the Centraalbureau voor Schimmelcultures at Baarn, The Netherlands, on Sep. 7, 1990, under number CBS 361.90.

MATERIALS AND METHODS

Cell Cultures and Viruses.

The CAV isolates were cultured in transformed lymphoblastoid cell lines from tumors of chickens induced by the avian leukosis virus of subgroup A (1104-X-5) or by Marek's disease virus (MDCC-MSB1). The cell cultures were infected with about 0.1-1 TCID50 per cell. After two days the cells were harvested. The cells were infected with virus progeny of cloned CAV DNA, or field isolates. CAV-Cux-4, originally isolated in Germany from a flock of chickens suffering from Marek's disease (Von Bülow et aL, (1983) *Zentralbatt für Veterinarmedizin* B 30:742–750; (1985) *Zentralbatt für Veterinarmedizin* B 32:679–693), was provided by Dr. M. S. McNulty, Veterinary Research Laboratories, Belfast, Northern Ireland. Two blood samples sent from the University of Delaware, Newark, U.S.A. were analyzed to determine the virulence of the Marek's disease strain T-1704 and its derivative, MDV-Del-S which is the first passage in a chicken. We obtained the CAV-T-1704 and CAV-Del-S isolates from SPF-chickens infected with the MDV-strain T-1704 and its derivative MDV-Del-S. The Dutch CAV isolates were aselectively selected from a series of sixty which were all cultured in MDCC-MSB1 cell cultures. The field material was supplied by J. C. van den Wijngaard, Gezondheidsdienst Brabant at Boxtel and J. Naber, Gezondheidsdienst voor Pluimvee at Doorn, mainly because atrophy of the thymus was established during autopsy. CAV isolates obtained from our own SPF flocks were added to the series.

Isolation of Total DNA.

Virus and liver preparations were resuspended in 20 mM Tris HC1-pH 7.5, 2 mM EDTA, 0.2% SDS, 0.6 mg/ml Proteinase-K and incubated for 1 hour at 37° C. The preparations were extracted with phenol-chloroform-isoamyl alcohol (25:24:1), and the DNA was precipitated by means of ethanol. The DNA pellets were resuspended in 100 $\mu$l 10 mM Tris HC1-pH 7.5, 1 mM EDTA.

Extraction and Analysis of Low Molecular Weight DNA.

Low molecular weight DNA was isolated from CAV-infected 1104-X5 and MDCC-MSB1 cells and uninfected 1104-X5 cells according to the method described by Hirt ((1967) *J. Molecular Biology* 26:365–369). The DNA was separated on agarose gels and, after staining with ethidium bromide, directly analyzed by means of UV light or blotted on a Biotrace filter according to the method described by Southern ((1982) *J. Molecular Biology* 98:503–517). The blots were hybridized with random-primed $^{32}$P-labelled DNA, isolated from low molecular weight DNA of CAV-infected 1104-X5 cells having a length of 2.7–3.5 kb.

Cloning of CAV DNA.

The entire CAV DNA genome was cloned in the bacterial vector pIC-20H. Parts of the CAV DNA genome were cloned in the vector pIC-19R. All plasmid DNA cloning steps were carried out in principle according to the methods described by Maniatis et al., ((1982) Molecular Cloning: A Laboratory Manual, New York, Cold Spring Harbor Laboratory).

Sequence Analysis of CAV DNA.

CAV DNA plasmids were purified by means of a CsCl-gradient and Sephacryl-S500 (Pharmacia) chromatography. Double-stranded DNA was sequenced by means of $T_7$ DNA polymerase (Pharmacia), or by means of Taq DNA polymerase (Promega). Both methods were conducted according to the instructions given by Pharmacia or Promega. The oligonucleotides were kinated with $T_4$ nucleotide kinase of Pharmacia. "Strong stops" were sequenced according to the method described by Maxam and Gilbert ((1977) *Proc. Nat'l. Acad. Sci.* (U.S.A.) 74:560–564).

Circularization of the Cloned CAV DNA Genome.

10 $\mu$g plasmid DNA of clones containing the entire CAV DNA genome were digested with restriction enzyme so that the entire CAV DNA insert was separated from the vector DNA. $T_4$-DNA ligase treatment of the 2.3 kilobase pairs of linear CAV DNA molecule resulted in a circular double-stranded CAV DNA. The ligation products were analyzed on a 0.8% agarose gel.

DEAE-Dextran Transfection.

For the transfection of 1104-X5 and MDCC-MSB1 cells 2 $\mu$g religated CAV DNA were suspended twice in 25 $\mu$l Milli-Q water and mixed with 260 $\mu$l TBS buffer. 15 $\mu$l 10 mg/ml DEAE-dextran was added to the DNA mixture, and the mixture was incubated for 30 minutes at room temperature.

1104-X5 cells. A 50 mm tissue culture plate with 1–2×$10^6$ 1104-X5 cells/plate was washed twice with TBS buffer. The TBS buffer was completely removed from the cell monolayer, and 300 $\mu$l DEAE-dextran/DNA-dilution were added. The cells were incubated for 30 minutes at room temperature. The DEAE-dextran/DNA-mix was replaced by 2 ml 25% DMSO/TBS, and the cell monolayer was incubated for 2 minutes at room temperature. The cells were washed twice with TBS buffer, and then tissue culture medium (RPMI1640 or E-MEM) was added. The cells were incubated at 37° C.–5% $CO_2$.

MDCC-MSB1 cells. About 2×$10^6$ MDCC-MSB1 cells were centrifuged at 1500 rpm in a table centrifuge. The medium was replaced by 5 ml TBS buffer, and the cells were carefully resuspended. The washing step was repeated. All TBS buffer was removed, the cell pellet was carefully resuspended in 300 $\mu$l DEAE-dextran/DNA-mix and incubated at room temperature for 30 minutes. 0.5 ml 25% DMSO/TBS were added, and the suspension was incubated for 3 minutes at room temperature. 5 ml TBS were added, and the cells were centrifuged at 1500 rpm in a table centrifuge. The supernatant was removed, and 50 ml tissue culture medium were added. The cells were resuspended and centrifuged off. The cells were received in 5 ml tissue culture medium and incubated at 37° C.-5% CO2. By way of control, 2 $\mu$g pIc-20H plasmid were used for transfection.

In Vitro Neutralization Test.

MDCC-MSB1 cells were infected with supernatant of MDCC-MSB1, and 1104-X5 cells were transfected with cloned "CAV DNA". About 2×$10^4$ cells were infected. The virus content of this inoculum was not exactly known. In half of the infected cell cultures polyclonal serum having a neutralizing activity directed against CAV, diluted 1:100, was added to the medium. By way of control, a series of "wells" with CAV-infected MSB1 cells was taken along, no antiserum directed against CAV being added to the medium.

CAV Infection of Day-Old Chicks.

Supernatants of CAV DNA and control DNA transfected MDCC-MSB1 and 1104-X5 cells were injected intramuscularly into day-old chicks. Six days after infection an autopsy was conducted at 5 chicks per group, after the hematocrit value and the total body weight had been determined first. For virus isolation and immunohistochemistry, heparin blood, thymus, and bone marrow were collected. The immunohistochemical research occurred by means of a peroxidase staining of thymus coupes with, inter alia, the CAV-specific monoclonal CV 1–85.1. Fourteen and twenty-eight days after infection an autopsy was conducted on 5 chicks per time point, and all the above determinations were carried out.

Polymerase Chain Reaction (PCR).

The oligonucleotides were synthesized by means of a Cyclone DNA synthesizer (Biosearch Inc. USA). The sequence was derived from the CAV DNA sequence shown in FIG. 1 (SEQ ID NO. 1). The PCR was isolated on DNA from CAV-infected and uninfected MDCC-MSB1 cells. The final concentration of the reagents were: 50 mM KCl, 10 mM Tris-HCl (pH 8.3), 3 mM $MgCl_2$, 0.01% calf serum albumin, 200 μM of each dNTP, 1 μM of each oligonucleotide and 2 units of Taq-DNA polymerase (Cetus, USA) in total 100 μl. The DNA samples were cyclically incubated 30 times at 93° C. for 1 minute, at 55° C. for 1 minute, and at 72° C. for 3 minutes in a Perkin Elmer/Cetus thermal cycler. One tenth of the amplified DNA was directly analyzed on a 2% agarose/ethidium bromide gel, or by Southern blot analysis. The DNA probe used was the oligonucleotide that was terminally labelled with $^{32}P$ according to Maniatis et al., (1982), supra.

Dot Blot Analysis.

The CAV DNA insert of pIC-20H/CAV-EcoRI was isolated and labelled with digoxigenin-11dUTP (Boehringer, Mannheim, Germany) according to the protocol of the supplier. Biotrace-RP filters were saturated with 1.5 M NaCl and 0.15 M Na citrate. The DNA samples were resuspended in 10 mM Tris HCl (pH 7.5) and 1 mM EDTA, boiled for 3 minutes, cooled on ice and placed on the filter. The filter was dried at room temperature and incubated for 30 minutes at 65° C. The filters were hybridized with digoxigenin-labelled DNA. The DNA labelled with digoxigenin was made visible by means of an immunological staining according to the protocol of the supplier.

EXAMPLE 1

Analysis of Low Molecular DNA Isolated from CAV-Infected Cells

The CAV genome isolated from a purified virus preparation proved to be a circular single-stranded DNA molecule having a length of about 2300 bases (Todd et al., (1990) *J. General Virology* 71:819–823. Our expectation was that in CAV-infected cells, in addition to circular single-stranded virus DNA, circular double-stranded CAV-DNA also occurs. Double-stranded DNA can be cut with restriction enzymes and therefore can be directly cloned, in contrast to single-stranded DNA. In view thereof, it was examined whether in the low molecular weight fraction of CAV-infected cells a DNA product occurs which was absent in uninfected cells.

Low molecular weight DNA was isolated from CAV-infected MDCC-MSB1 and 1104-X5 cells and from uninfected 1104-X5 cells. The DNA was fractionated on an agarose/ethidium bromide gel. A very weak DNA band having a (measured) length of about 3 kilobase pairs (kbp), was visible in the gel. This specific DNA product was absent in the DNA isolated from uninfected cells.

In the following experiment it was made more probable that the specific DNA was only present in CAV-infected cells. DNA isolated from infected cells was separated by length by means of an agarose gel. DNA having a length of 2.7–3.5 kbp was isolated. This DNA fraction contains the specific virus DNA, in addition to other cellular DNA. The isolated DNA was radioactively labelled and hybridized with a Southern blot of low molecular DNA from CAV-infected cells and from uninfected cells. At the height of 3 kbp a DNA product hybridized in the blot of CAV-infected cells which was absent in the DNA blot of uninfected cells.

The length of 3 kbp was determined with DNA markers consisting of double-stranded linear DNA molecules. The behavior of a circular double-stranded DNA molecule in an agarose gel is different from that of linear DNA fragments. The DNA of 3 kbp from CAV-infected cells could be a linear form of a DNA which, in reality, is 2.3 kbp in length. If the circular double-stranded DNA is digested with a restriction enzyme cutting only once into the DNA molecule, a linear DNA molecule having a (measured) length of 2.3 kbp must be formed. That this assumption is correct, was demonstrated by separately incubating low molecular DNA isolated from CAV-infected 1104-X5 cells with six different restriction enzymes (BamHI, EcoRI, HindIII, KpnI, PstI, and XbaI). A Southern blot of low molecular DNA isolated from CAV-infected 1104-XS cells and cut with the above restriction enzymes was hybridized with the above radioactively labelled DNA probe. This showed that treatment with the restriction enzymes BanHI, EcoRI, PstI, and XbaI resulted in a DNA molecule having a measured length of 2.3 kbp. DNA of uninfected cells incubated with BamHI did not contain this DNA product. The restriction enzyme HindIII cut twice into the DNA, while KpnI did not cut. It can be concluded from the above experiments that in low molecular weight DNA of CAV-infected cells a 2.3 kbp circular DNA molecule occurs which is absent in uninfected cells and that this is the CAV genome in the form of a circular double-stranded DNA molecule.

EXAMPLE 2

Cloning and Subcloning of Double-Stranded CAV-DNA in a Bacterial Vector

Low molecular weight DNA of CAV-infected 1104-X5 cells was separately incubated with BamHI, EcoRI, PstI, and XbaI. The DNA was separated on a low melting point agarose gel. From all four DNA preparations the 2.3 kbp DNA molecule was isolated. The cloning vector pIC-20H was separately digested with the same four restriction enzymes with which the low molecular weight DNA was cut. The linear vector was treated with calf intestine alkaline phosphatase. Each 2.3 kbp DNA fragment was ligated at the corresponding restriction enzyme site of pIC-20H. The ligation products were transfected in the *E. coli* strain HB101. All 4 clonings gave plasmids containing inserted DNA having a length of about 2.3 kbp. A further restriction enzyme analysis showed that at least 7 plasmids contained the same DNA fragment. The place of integration of the vector, however, was different because of the use of different enzymes to cut open the circular molecule. By means of the restriction enzymes BamHI, EcoRI, PstI, and XbaI a restriction enzyme map was determined of all four CAV DNA clones.

Four "different" CAV DNA plasmids were radioactively labelled and hybridized with Southern blots of BamHI-digested DNA isolated from CAV-infected and uninfected cells. All tested clones hybridized only with the 2.3 kbp DNA molecule present in DNA of CAV-infected cells.

EXAMPLE 3

Biological Activity of Two CAV DNA Clones

The two CAV clones pIC-20H/CAV-EcoRI and pIC-20H/CAV PstI were digested with restriction enzymes so that the CAV DNA was entirely cut from the vector. The linear CAV DNA molecules were treated with $T_4$-DNA ligase. The linear CAV DNAs were thus circularized. The "cloned" CAV DNA now had the double-stranded circular form also possessed by wild-type CAV DNA in infected cells. MDCC-MSB1 and 1104-X5 cells were transfected with the "cloned" circular CAV DNAs. For clone pIC-20H/CAV-EcoRI a very clear cytopathogenic effect (CPE) was found in both cell types. Clone pIC-20H/CAV-PstI caused a clear CPE in MDCC-MSB1 cells and a less clear CPE in 1104-X5 cells. However, the supernatants of pIC-20H/CAV-PstI transfected 1104-X5 cells caused a clear CPE in MDCC-MSB1 cells. Transfections with DNA isolated from CAV-infected cells also caused a clear CPE in MDCC-MSB1 cells, while in 1104-X5 cells a less clear CPE was to be seen. The CPE was not obtained after transfection of MDCC-MSB1 or 1104-X5 cells with pIC-20H vector DNA.

A Southern analysis showed that in cell lysates of MDCC MSB1 and 1104-X5 cells infected with virus (passage 6), obtained by cloned CAV DNA, CAV DNA was present. A neutralization test with MDCC-MSB1 cells showed that the CPE caused by cloned DNA in the transfected cells was the result of a CAV infection. Neutralizing antibodies directed against CAV prevented the CPE of MDCC-MSB1 cells infected with CAV progeny of transfected cells.

Day-old chicks were injected intramuscularly with supernatant of transfected cells. In the chicken the supernatants caused the same clinical image as wild-type CAV: retarded growth appearing from differences in the total body weight, pale bone marrow and reduced hematocrit values (anemia), thymus atrophy (depletion of a specific population of T cells) and mortality. Supernatants of cells transfected with vector DNA caused no disease symptoms in the control chicks.

EXAMPLE 4

Sequence Analysis of the Double-Stranded CAV DNA Genome

The entire double-stranded CAV DNA genome was completely sequenced by means of the Sanger method (Sanger, et al., (1977) *Proc. Nati. Acad. Sci.* (USA) 74:5463–5467) and the Maxam-Gilbert method. By means of the M13 sequencing and M13-reverse sequencing primers the DNA sequence of about 2100 bases was determined of the 4 pIC-20H/CAV (BamHI, EcoRI; PstI; XbaI) clones. Then the CAV genome was subcloned. Of the five different subclones of the CAV DNA genome the DNA sequence was determined by the Sanger method by means of the M13 primers and/or the Maxam-Gilbert method. Thus the DNA sequence of both strands of the CAV genome was determined.

The length of the CAV (double-stranded) DNA is 2319 bp. The first base of the EcoRI site of the circular CAV genome is numbered +1. The sequence of the DNA strand containing most of the largest open reading frames is shown in FIG. 1 and is called (+) strand. The composition of the bases of this strand is: 25.5% adenine; 28.7% cytosine; 27.7% guanine; 18.1 % thymine. Computer studies into possible homology of the CAV genome with already known virus sequences showed that the DNA was not described before and did not form part of an earlier described virus group. The initial hypothesis that CAV is a parvovirus is no longer sound as far as sequence and form of the CAV DNA genome (circular) are concerned.

By means of computer studies the organization of the CAV genome was characterized. The open reading frames, promoter/enhancer elements, polyadenylation signal and site, and "origin of replication" are predicted. FIG. 2 shows the predicted open reading frames, exceeding 300 bases, for both DNA strands of CAV. FIG. 2A shows the open reading frames beginning with the codon ATG. The ATG codon is the most frequently used initiation codon for proteins. It is remarkable that one of both DNA strands codes for 3 proteins having a length of 449 amino acids (51.6 kDa), 216 amino acids (24 kDa), and 121 amino acids (13.3 kDa). Todd, et al. ((1990) *J. General Virology* 71:819–823)) showed a 50-kDa protein in purified CAV. If all the open reading frames are actually used, about 80% of the virus genome is translated into protein. Some regions even double. It is quite possible that the three open reading frames are translated from one RNA. The predicted start of the RNA molecule is at position 354 and the poly(A) addition at position 2317. The only poly(A) signal is at position 2287 of the plus strand.

Figure 2B:
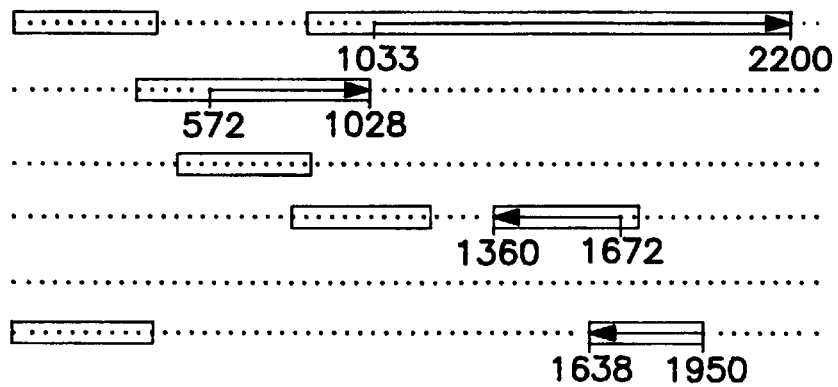
FIGS. 2B and 2C show open reading frames using respectively CTG and GTG as a start codon.
Figure 2C:
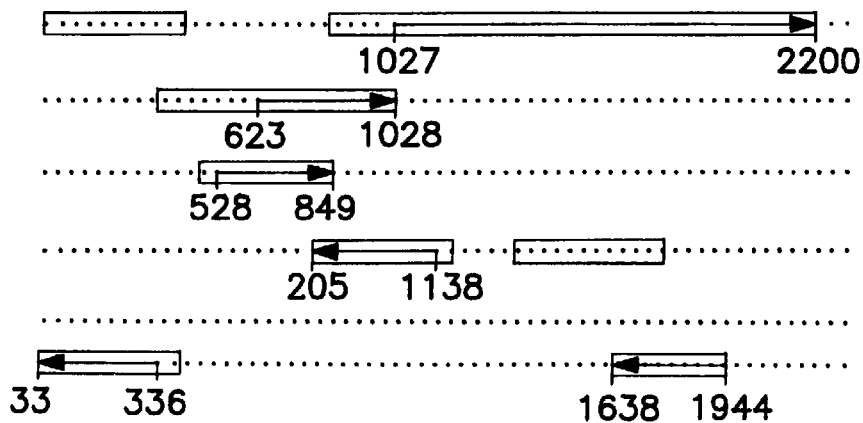

It is unlikely that the open reading frames are used at the other DNA strand because this strand lacks some essential regulation sequences. FIGS. 2B and 2C show open reading frames using respectively CTG and GTG as a start codon. However, it is described for only a few proteins that these start codons are actually used (Hann, et al., (1988) *Cell* 52:185–195).

Computer studies into similarities between the separate CAV proteins and already known proteins gave only limited homologies on sequences present in the available programs. Accordingly, it is hard to predict what type of protein the CAV proteins resemble. A relatively high score was made by viral capsid, DNA-binding and blood coagulation proteins. The results are not given here.

The expression of proteins is regulated by promoter/enhancer elements (Jones, (1990) *Seminars in Career Biology* 1:5–9). An eukaryotic promoter is mostly positioned right before the start of the transcript. The CAV sequence contains upstream of the cap site the general elements: TATA box, SP1 box, and CAAT box. The sequence and the position of these boxes excellently correspond with those described in most of the eukaryote promoters (Table 1). Around position 285 there may be binding sites for four different transcription factors: CREB, MLTF, GT, and PEA-I.

TABLE 1

Known transcription factor binding sequence elements
in the enhancer/promoter region of CAV

| | Element | Consensus sequence | CAV sequence | Position in CAV sequence |
|---|---|---|---|---|
| 1. | —TATA—# | GTATA$^A$/$_T$A$^A$/$_T$ | GTATATAT | 321–330+ |
| 2. | SP1 | GGGCGG | GGGCGG | 305–310+ |
| 3. | CREB | TGACGTCA | TGACGTTT | 290–297 |
| 4. | PEA—I$^{(Py)}$ | GGAAG<u>TGACTA</u>AC (SEQ ID NO. 6) | GAAAG<u>TGAC</u>TTTC (SEQ ID NO. 7) | 286–298 |
| 5. | GT$^{(SV40)}$ | G$^C$/$_T$TGTGGAA$^A$/$_T$GT (SEQ ID NO. 8) | CGTTGCGAAAGT (SEQ ID NO. 9) | 279–290 |
| 6. | MLTF | GGCCACGTGACC (SEQ ID NO. 10) | TGCCACTGTCGA (SEQ ID NO. 11) | 274–285 |
| 7. | CCAAT—TF | AGCCAAT | AGCCAAT | 260–266+ |
| 8. | —CACCC—# | CACCC | CAGCC | 259–263 |
| 9. | ATF | ACGTCA | ACGTCA | 253–258+ |
| 10. | —CACCC—# | CACCC | CAGCC | 236–240 |
| 11. | ATF | ACGTCA | ACGTCA | 232–237+ |
| 12. | SP1$^{(weak)}$ | | GAGGCG | 209–214 |
| 13. | ATF | ACGTCA | ACGTCA | 199–204+ |
| 14. | —CACCC—# | CACCC | CATCC | 182–186 |
| 15. | ATF | ACGTCA | ACGTCA | 178–183+ |
| 16. | —CACCC—# | CACCC | CATCC | 161–165 |
| 17. | ATF | ACGTCA | ACGTCA | 157–162+ |

—CAP site is probably at about 350
+perfect homology between CAV and consensus sequence
__consensus sequence found in several viruses
DNA sequence of an element An eukaryote gene also contains enhancer elements determining the strength of the eukaryote promoter. Possible enhancer elements are the five direct repeats all having a length of 21 nucleotides and being located between positions 144 and 260. All repeats have 19 identical nucleotides. Only the last 2 nucleotides are different. Repeat 1 is identical with 2, and 3 is equal to 5. Repeats 1, 2, and 3 are located beside each other, like 4 and 5. Located between repeats 3 and 4 is a "break" of 12 nucleotides. A computer study shows that no (eukaryote) enhancer described contains all sequences found for the probable CAV enhancer elements. All direct repeats contain an ATF element which may be involved in the increase in the transcription of CAV RNAs. The direct repeats contain twice the sequence CATCC and twice the sequence CAGCC. The last sequence overlaps with the CAAT box. These four sequences only have 1 mismatch with the CACCC box described for β-globin (Table 1).

Figures 3A, 3B, 3C:
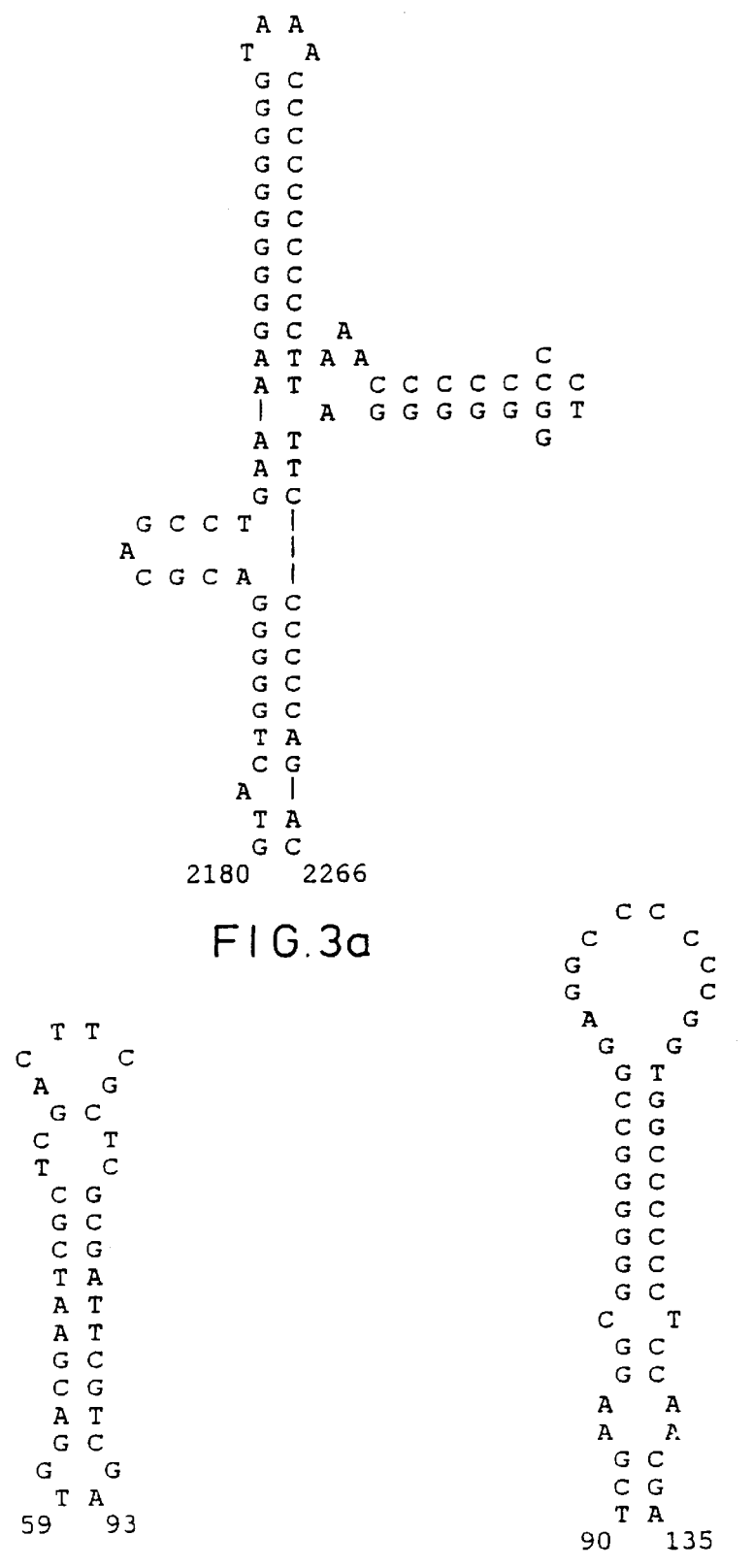

FIG. 3 shows that approximately between positions 55 and 135 (SEQ ID NO. 4–5) and between positions 2180 and 2270 (SEQ ID NO. 3) of the plus DNA strand very large hairpin structures are present in the (single-stranded) DNA form of CAV. Hairpin structures in the DNA may be involved in the replication of the CAV DNA. The hairpins between 2180 and 2270 may be present not only in CAV DNA but also in CAV RNA and are likely to play a role in the stability of the CAV RNA.

EXAMPLE 5

Analysis of CAV DNA

The Different DNA Forms of CAV in Infected Cells

Four different CAV DNA molecules are visible in a Southern blot of a DNA preparation of CAV-infected cells. The DNA was hybridized with radioactively labelled DNA of clone pIC-20H/CAV-EcoRI. The CAV DNA molecules are, in view of their measured lengths and forms in a non-denaturing agarose gel and susceptibility to s1 nuclease, respectively double-stranded open circles (3 kbp), supercoiled double-stranded DNA (2 kbp), circular single-stranded DNA (0.8 kbp) and single-stranded linear DNA 1.5 kbp). Sometimes the linear double-stranded DNA form of CAV is also visible (2.3 kbp). Todd, et al., ((1990) *J. General Virology* 71:819–823) have measured a length of 0.8 kbp for the circular single-stranded DNA from isolated CAV on the basis of the electrophoretic mobility in a non-denaturing agarose gel.

Detection of CAV DNA in Virus Preparations.

Total DNA was isolated from CAV and purified according to the method described by Von Bülow. The DNA preparation was analyzed in a Southern assay with a labelled CAV DNA probe containing the entire cloned CAV sequence. DNA isolated from purified CAV contains a DNA molecule having a length of 0.8 kbp, measured in a non-denaturing agarose gel. In a Southern analysis of DNA isolated from purified CAV, with oligonucleotides derived from the cloned CAV DNA sequence as probes, it was demonstrated that the minus DNA strand is enclosed in the virus. From this it may be concluded that the single-stranded DNA of CAV in the capsid is the minus strand.

Southern Analysis of DNA from CAV Field Isolates.

DNA preparations were prepared from CAV isolates obtained from chickens from flocks in which Marek's disease occurred to an increased extent. The DNA preparations from CAV isolates obtained in 12 companies in the Netherlands were collected a selectively from a collection of 60 samples. In only one company a higher mortality owing to Marek's disease was reported. Moreover, a CAV isolate originated from a guinea fowl. The CAV isolates examined by us were chiefly obtained after atrophy of the thymus was established upon examination by the Animal Health Services.

For the purpose of studying the degree of similarity between cloned CAV DNA (pIC-20H/CAV-EcoRI) and DNA of the different CAV field isolates MDCC-MSB1 cells were infected with the isolated CAV strains. A Southern analysis was conducted. All DNA preparations contained DNA molecules that specifically hybridized with $^{32}$P-labelled cloned CAV DNA. The DNA molecules of the different CAV field isolates have lengths corresponding to that of the cloned CAV and are double-stranded or single-stranded. Southern blot analyses directly conducted on tissue samples of the CAV-infected chickens from the field were found to contain DNA molecules that hybridized with labelled pIC-20H/CAV-EcoRI.

Restriction Enzyme Analysis of DNA from CAV Field Isolates.

Figure 5:
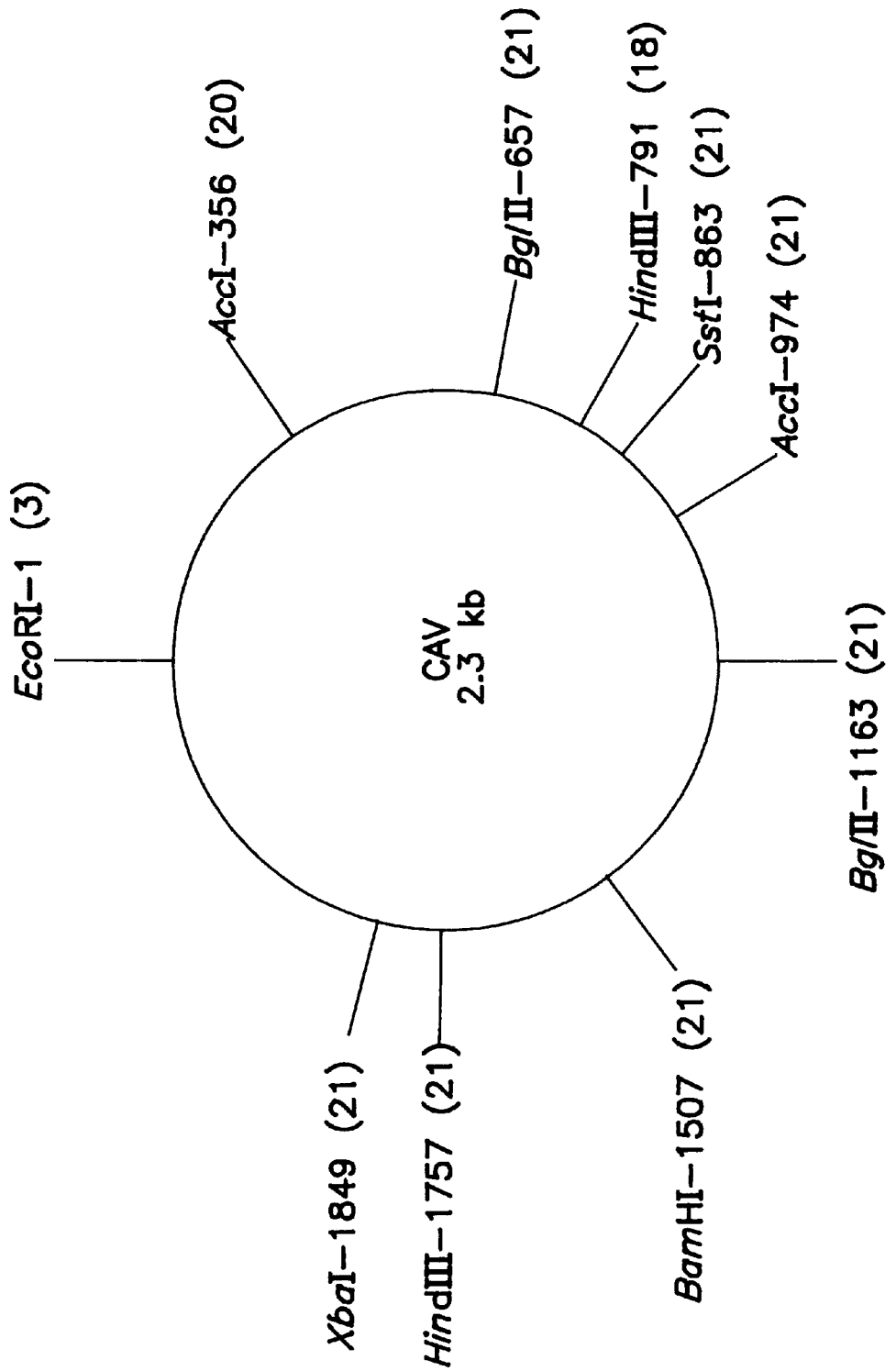
FIG. 5 shows the restriction enzyme map of the cloned CAV DNA. Summarized are the restriction enzyme maps of the cloned CAV and the different field isolates. Per restriction enzyme site, the number of field isolates containing the relevant site are bracketed.
Figures 6A, 6B:
FIG. 6 (SEQ ID NOS: 12–21) shows a schematic representation of the positions of the five different direct-repeat units and the 12-bp insert.

The similarity of DNA from the different CAV field isolates with the cloned CAV genome was further examined by means of restriction enzyme analysis. The DNA preparations of the CAV isolates and of cloned CAV were separately cut with seven restriction enzymes. The enzymes BanHI, BglI, SstI, and XbaI proved to cut all DNAs identically. DNA of most of the field isolates contained two AccI sites and/or two HindIII sites, while DNA of only a few isolates contained the EcoRI site. FIG. 5 summarizes the restriction enzyme maps of the cloned CAV and the different field isolates. Per restriction enzyme site the number of field isolates containing the relevant site are bracketed.

Polymerase Chain Reaction (PCR) of DNA from CAV Field Isolates.

The oligonucleotides CAV-1 and CAV-2 (FIG. 4) (SEQ ID NO. 2), derived from the cloned CAV DNA sequence were synthesized. PCR using these synthetic oligonucleotides was conducted to specifically detect DNA from CAV in the field. DNA isolated from MDCC-MSB1 cells infected with the different CAV isolates and DNA isolated from uninfected cells was amplified. After DNA amplification the DNA was electrophoretically separated to length on an agarose/ethidium bromide gel. An amplified 186 bp band (i.e. The value theoretically expected) was visible in all DNA samples of cells infected with the different CAV isolates. This specific band was not present after amplification of DNA isolated from uninfected cells. Amplified DNA bands of all field isolates show an identical rate of migration in the agarose gel. This result implies that no great deletions or insertions occur in this part of the genome of the different CAV field isolates. A Southern analysis with the $^{32}$P-labelled oligonucleotide CAV-3 (FIG. 4) (SEQ ID NO. 2) showed that the 186 bp amplified DNA is CAV-specific and that no other DNA band hybridized with the CAV-3 probe.

The susceptibility of detection of the CAV PCR was examined. DNA was isolated from CAV-infected cells, diluted stepwise, amplified and analyzed on an agarose/ethidium bromide gel. After amplification of samples containing an amount of DNA corresponding to the amount of DNA in about 100 CAV-infected cells, a CAV-specific DNA fragment of 186 bp was detected. However, if the amplified DNA was subjected to a Southern analysis with $^{32}$P-labelled CAV-3 DNA, an amount of DNA corresponding to DNA from 1 cell was already found to result in a clearly visible CAV-specific DNA band. The CAV PCR is a very sensitive detection method which is specific for the hitherto examined CAV isolates.

EXAMPLE 6

Dot Blot Analysis of DNA from CAV Field Isolates With Digoxigenin-Labelled CAV DNA Probes In addition to the PCR, an assay was developed for the detection of DNA from CAV field isolates. This test does not use radioactive probes. The CAV DNA insert of clone pIC0H/CAV-EcoRl was labelled with 11-dUTP-digoxigenin. DNA preparations from MDCC-MSB1 cells, separately infected with the different CAV isolates, were blotted on a filter and analyzed for their ability to hybridize with the digoxigenin-labelled DNA probe. DNA preparations from MDCC-MSB1 cells infected with the different CAV isolates hybridized with the digoxigenin-labelled DNA probe, while DNA from uninfected cell cultures did not hybridize. This test using a non-radioactively labelled CAV DNA probe is therefore suitable for detection of DNA from CAV field isolates.

APPLICATIONS

DNA.

CAV sequences of, e.g., the pIC-20H/CAV-EcoRI DNA plasmid or parts thereof can be used to demonstrate CAV DNA and/or RNA in preparations to be examined for research and diagnostics purposes. The DNA may be labelled radioactively or in another manner, e.g., with biotin/digoxigenin. By means of DNA/RNA slot blots, Southern/Northern analyses and in vitro hybridizations the presence of CAV nucleic acids can be established. Parts of the CAV sequences as used herein are also DNA'oligomers.

Oligomers derived from the CAV sequences of clone pIC-20H/CAV-EcoRI can be used in a "Polymerase Chain Reaction" to trace very low concentrations of CAV DNA/RNA. The PCR is a very sensitive method frequently used for the detection of viruses.

Diagnostic kits based on the above applications are possible in practice.

For research purposes techniques like S1 mapping and primer extension with the CAV DNA fragments are important. By these two methods, CAV RNA can be quantified and further characterized.

Oligomers in antisense configuration can be used to study gene functions. These may also serve as a model for studying novel methods of inhibiting virus replication.

CAV DNA may be used as a carrier in the transfection for small gene fragments, particularly if the pathogenic properties have been removed by deletion in the CAV genome.

CAV oligomers in antisense configuration may be expressed in virus vectors, which enables studying CAV replication or other gene functions in the living animal or in vitro.

RNA.

CAV DNA fragments cloned in Sp6/T7 vectors result in CAV RNA products. CAV RNAs obtained by in vitro transcription can be used for in vitro/in vivo synthesis of CAV proteins. Thus, RNA molecules, e.g. in a wheat germ extract, can be translated into proteins (in vitro translation). The CAV proteins obtained by in vitro translation may then be used, e.g., for tracing antibodies directed against CAV in sera of chickens (see below). CAV RNA molecules may also be forced into cells by micro-injection to be translated therein into proteins. Thus, the effects of CAV proteins can be studied on a cellular level. Protein/protein and/or protein/DNA interactions also can be analyzed.

CAV RNAs also can be used as probes for tracing CAV nucleic acids in preparations. The analyses can be conducted by means of slot blot, Southern, Northern and in situ hybridization analyses. These methods can be used to develop diagnostic tests for CAV.

Proteins.

All CAV proteins can be expressed in prokaryote or in eukaryote systems. This requires the CAV open reading frames found to be cloned in a suitable expression vector. For the bacterial system there is an expression vector based on the T7 promoter suitable for the expression of CAV open reading frames. The baculovirus system, yeast, and the CHO-dhfr system are possible eukaryote expression systems. Viral vectors, such as retroviral vectors, are also eligible therefor.

The CAV proteins or epitopes located thereon can be used to trace antibodies directed against CAV. Thus, CAV-infected chickens can be traced. The CAV proteins or epitopes located thereon can be used in immunoassays, such as immunoperoxidase stainings, ELISAs and immunofluorescence assays.

The CAV proteins or epitopes located thereon can be used to provide humoral and/or cell-bound immunity against CAV. The CAV proteins obtained by expression in eukaryote and prokaryote vector/host systems can be used for use in subunit vaccines.

By means of the CAV proteins or epitopes located thereon CAV-specific antibodies can be obtained which enables CAV proteins to be traced in preparations of CAV-infected chickens (see below).

Antibodies.

In a number of infection tests in young chicks it could be confirmed that maternal antibodies can provide effective passive protection against CAV infection. The maternal antibodies were transmitted to the young chicks via the natural route, as well as via injection of newly born chicks with CAV antibody containing egg yolk extracts. Passive protection against a CAV infection was also provided by means of injection of egg yolk extracts of eggs from laying hens which had been infected with CAV just before the egg laying period. Vaccination of laying hens with CAV proteins expressed in one of the above expression systems will result in the formation of maternal antibodies. Young chicks of these laying hens will be protected Against CAV infection.

Diagnostic tests can be developed on the basis of antibodies against CAV. Both polyclonal and monoclonal antibodies may be used therefor. By means of CAV-specific antibodies, preparations can be examined for the presence of CAV proteins.

The above applications of CAV antibodies are possible for antibodies according to the invention, obtained by processes as described therein, in the same manner as for natural CAV antibodies.

Living Virus Vaccines.

Providing the immune system with viral proteins by means of a living virus vector is likely to result in a better immune response than a subunit vaccine. One or more CAV open reading frames (in whole or in part) could be cloned in living virus vectors. In poultry there can only be used living virus vectors that themselves show a good replication in the avian system. Eligible as vectors for application in the chicken are, e.g.: fowl pox virus, retroviral vectors, herpesvirus vectors (avian herpesvirus serotypes 1, 2, and 3) and infectious laryngotracheitis virus, and possibly also adenoviruses such as CELO. Immunization with the above living virus vectors protects against CAV and the carrier virus.

By means of applying one or more deletions in the CAV genome there may be developed vaccines that immunize against CAV infection in young chicks. When applying the deletions the pathogenic character of CAV infection must be eliminated but the replicative and therefore immunizing properties must be retained.

The CAV genome can also itself be made suitable as a living virus vector for the expression of antigens of other viruses. This requires the CAV genome to be changed such that in addition to or instead of CAV proteins "foreign" virus proteins are expressed. CAV vectors therefore can be constructed such that protection occurs against "foreign" viruses alone or also against CAV, depending on the expression of the viral proteins by the recombinant vector in the vaccinated animal.

CAV vaccines produced as a subunit vaccine, a deletion vaccine or a gene fragment or a gene fragment in another virus vector will chiefly be used for the vaccination of laying hens. However, vaccination of chicks at a younger age, e.g. in combination with a vaccination against Marek's disease, also remains a possible use of the invention.

Enhancer/Promoter Elements.

The CAV promoter and enhancer elements can be cloned in DNA vectors. Under the regulation of the CAV promoter/enhancer CAV proteins or "foreign" proteins can be expressed in both chicken cells and in other cell types.

It is conceivable that the CAV promoter is functional in (chicken) bone marrow cells. As a model system for gene therapy "foreign" proteins can be expressed in vitro in bone marrow cells by genes of CAV promoter/enhancer elements, optionally in combination with retroviral vectors. The genetically modified bone marrow cells may then be transplanted into the bone marrow of, in the present case, the chicken. For very small gene fragments the CAV genome itself is also eligible for use as a vector.

The CAV enhancer/promoter elements could also be active in other organisms. If this should be the case, the elements can also be used in, e.g., the mouse system as a model for gene therapy.

Products of CAV itself under the regulation of our own CAV promoter or another promoter also provide possibilities for studying and developing techniques for gene therapy.

The possibility of using the entire or substantially the entire CAV genome as a cloning vector, i.e. as a kind of eukaryotic plasmid for avian systems, is a development that is to be considered real in view of the discovered structure of the CAV genome.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. An isolated CAV protein or part thereof which is immunogenic, obtained by in vitro translation of SEQ ID NO:26 or a nucleotide sequence coding for a CAV protein selected from the group consisting of VP2 and VP3, or part thereof.

2. A CAV protein or part thereof which is immunogenic, obtained by isolation from a prokaryotic or eukaryotic cell expressing SEQ ID NO:26 or a nucleotide sequence consisting essentially of an open reading frame coding for a CAV protein selected from the group consisting of VP2 or VP3 or part thereof.

3. A recombinant CAV protein encoded by a nucleic acid having a nucleotide sequence depicted in SEQ ID NO:26.

4. A recombinant CAV protein encoded by a nucleic acid having a nucleotide sequence depicted in SEQ ID NO:27.

5. A recombinant CAV protein encoded by a nucleic acid having a nucleotide sequence depicted in SEQ ID NO:28.

6. A CAV protein or part thereof which is immunogenic, obtained by in vitro translation of a nucleotide sequence coding for a CAV protein, wherein said nucleotide sequence is selected from the group consisting of SEQ ID NO:26, SEQ ID NO:27 and SEQ ID NO:28.

7. A CAV protein or part thereof which is immunogenic, obtained by isolation from a prokaryotic or eukaryotic cell expressing a nucleotide sequence coding for a CAV protein, wherein said nucleotide sequence is selected from the group consisting of SEQ ID NO:26, SEQ ID NO:27 and SEQ ID NO:28.

8. A diagnostic kit for detecting CAV-specific antibodies in an immunoassay process, said diagnostic kit containing a CAV protein or protein part according to any one of claims 1 or 2 as a reagent for binding said CAV-specific antibodies.

9. A vaccine preparation for immunizing against CAV in a host in need thereof, said preparation comprising:

one or more CAV proteins according to any one of claims 1 or 2 and optionally one or more carriers and adjuvants suitable for subunit vaccines.

10. The diagnostic kit according to claim 8 wherein said immunoassay process is selected from the group consisting of an immunoperoxidase staining assay, an ELISA and an immunofluorescence assay.

11. A diagnostic kit for detecting CAV-specific antibodies in an immunoassay process, said diagnostic kit containing a CAV protein or protein part according to any one of claims 6 or 7 as a reagent for binding said CAV-specific antibodies.

12. A vaccine preparation for immunizing against CAV in a host in need thereof, said preparation comprising:

one or more CAV proteins according to any one of claims 6 or 7 and optionally one or more carriers and adjuvants suitable for subunit vaccines.

13. The diagnostic kit according to claim 11 wherein said immunoassay process is selected from the group consisting of an immunoperoxidase staining assay, an ELISA and an immunofluorescence assay.

* * * * *

SEQUENCE LISTING

```
(1) GENERAL INFORMATION:

(iii) NUMBER OF SEQUENCES: 28
```

(2) INFORMATION FOR SEQ ID NO: 1:

(i) SEQUENCE CHARACTERISTICS:
        (A) LENGTH: 2319 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
GAATTCCGAG TGGTTACTAT TCCATCACCA TTCTAGCCTG TACACAGAAA GTCAAGATGG      60
ACGAATCGCT CGACTTCGCT CGCGATTCGT CGAAGGCGGG GGGCCGGAGG CCCCCCGGTG     120
GCCCCCCTCC AACGAGTGGA GCACGTACAG GGGGGTACGT CATCCGTACA GGGGGGTACG     180
TCATCCGTAC AGGGGGGTAC GTCACAAAGA GGCGTTCCCG TACAGGGGGG TACGTCACGC     240
GTACAGGGGG GTACGTCACA GCCAATCAAA AGCTGCCACG TTGCGAAAGT GACGTTTCGA     300
AAATGGGCGG CGCAAGCCTC TCTATATATT GAGCGCACAT ACCGGTCGGC AGTAGGTATA     360
CGCAAGGCGG TCCGGGTGGA TGCACGGGAA CGGCGGACAA CCGGCCGCTG GGGGCAGTGA     420
ATCGGCGCTT AGCCGAGAGG GGCAACCTGG GCCCAGCGGA GCCGCGCAGG GGCAAGTAAT     480
TTCAAATGAA CGCTCTCCAA GAAGATACTC CACCCGGACC ATCAACGGTG TTCAGGCCAC     540
CAACAAGTTC ACGGCCGTTG GAAACCCCTC ACTGCAGAGA GATCCGGATT GGTATCGCTG     600
GAATTACAAT CACTCTATCG CTGTGTGGCT GCGCGAATGC TCGCGCTCCC ACGCTAAGAT     660
CTGCAACTGC GGACAATTCA GAAAGCACTG GTTTCAAGAA TGTGCCGGAC TTGAGGACCG     720
ATCAACCCAA GCCTCCCTCG AAGAAGCGAT CCTGCGACCC CTCCGAGTAC AGGGTAAGCG     780
AGCTAAAAGA AAGCTTGATT ACCACTACTC CCAGCCGACC CCGAACCGCA AAAAGGCGTA     840
TAAGACTGTA AGATGGCAAG ACGAGCTCGC AGACCGAGAG GCCGATTTTA CTCCTTCAGA     900
AGAGGACGGT GGCACCACCT CAAGCGACTT CGACGAAGAT ATAAATTTCG ACATCGGAGG     960
AGACAGCGGT ATCGTAGACG AGCTTTTAGG AAGGCCTTTC ACAACCCCCG CCCCGGTACG    1020
TATAGTGTGA GGCTGCCGAA CCCCCAATCT ACTATGACTA TCCGCTTCCA AGGGGTCATC    1080
TTTCTCACGG AAGGACTCAT TCTGCCTAAA AACAGCACAG CGGGGGGCTA TGCAGACCAC    1140
ATGTACGGGG CGAGAGTCGC CAAGATCTCT GTGAACCTGA AAGAGTTCCT GCTAGCCTCA    1200
ATGAACCTGA CATACGTGAG CAAAATCGGA GGCCCCATCG CCGGTGAGTT GATTGCGGAC    1260
GGGTCTAAAT CACAAGCCGC GGACAATTGG CCTAATTGCT GGCTGCCGCT AGATAATAAC    1320
GTGCCCTCCG CTACACCATC GGCATGGTGG AGATGGGCCT TAATGATGAT GCAGCCCACG    1380
GACTCTTGCC GGTTCTTTAA TCACCCAAAG CAGATGACCC TGCAAGACAT GGGTCGCATG    1440
TTTGGGGGCT GGCACCTGTT CCGACACATT GAAACCCGCT TTCAGCTCCT TGCCACTAAG    1500
AATGAGGGAT CCTTCAGCCC CGTGGCGAGT CTTCTCTCCC AGGGAGAGTA CCTCACGCGT    1560
CGGGACGATG TTAAGTACAG CAGCGATCAC CAGAACCGGT GGCAAAAAGG CGGACAACCG    1620
ATGACGGGGG GCATTGCTTA TGCGACCGGG AAAATGAGAC CCGACGAGCA ACAGTACCCT    1680
GCTATGCCCC CAGACCCCCC GATCATCACC GCTACTACAG CGCAAGGCAC GCAAGTCCGC    1740
TGCATGAATA GCACGCAAGC TTGGTGGTCA TGGGACACAT ATATGAGCTT TGCAACACTC    1800
ACAGCACTCG GTGCACAATG GTCTTTTCCT CCAGGGCAAC GTTCAGTTTC TAGACGGTCC    1860
TTCAACCACC ACAAGGCGAG AGGAGCCGGG GACCCCAAGG GCCAGAGATG GCACACGCTG    1920
GTGCCGCTCG GCACGGAGAC CATCACCGAC AGCTACATGT CAGCACCCGC ATCAGAGCTG    1980
```

```
GACACTAATT TCTTTACGCT TTACGTAGCG CAAGGCACAA ATAAGTCGCA ACAGTACAAG      2040

TTCGGCACAG CTACATACGC GCTAAAGGAG CCGGTAATGA AGAGCGATGC ATGGGCAGTG      2100

GTACGCGTCC AGTCGGTCTG GCAGCTGGGT AACAGGCAGA GGCCATACCC ATGGGACGTC      2160

AACTGGGCGA ACAGCACCAT GTACTGGGGG ACGCAGCCCT GAAAAGGGGG GGGGGCTAAA      2220

GCCCCCCCCC CTTAAACCCC CCCCTGGGGG GGATTCCCCC CCAGACCCCC CCTTTATATA      2280

GCACTCAATA AACGCAGAAA ATAGATTTAT CGCACTATC                             2319
```

(2) INFORMATION FOR SEQ ID NO: 2:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
ACCGGTCGGC AGTAGGTATA CGCAAGGCGG TCCGGGTGGA TGCACGGGAA CGGCGGACAA       60

CCGGCCGCTG GGGGCAGTGA ATCGGCGCTT AGCCGAGAGG GGCAACCTGG GCCCAGCGGA      120

GCCGCGCAGG GGCAAGTAAT TTCAAATGAA CGCTCTCCAA GAAGATACTC CACCCGGACC      180

ATCAACGGTG TTCAGGCCAC CAACAAGTTC                                      210
```

(2) INFORMATION FOR SEQ ID NO: 3:

(i) SEQUENCE CHARACTERISTICS:
        (A) LENGTH: 86 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 3:

```
GTACTGGGGG ACGCAGCCTG AANAAGGGGG GGGGGTAAAC CCCCCCCCCT TAAACCCCCC       60

CCTGGGGGGG ATTCNNCCCC CAGNAC                                           86
```

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 4:

```
TGGACGAATC GCTCGACTTC GCTCGCGATT CGTCGA                                36
```

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single
        (D) TOPOLOGY: circular (ii) MOLECULE TYPE: DNA (genomic)

(xi) SEQUENCE DESCRIPTION: SEQ ID NO: 5:

```
TCGAAGGCGG GGGGCCGGAG GCCCCCCGGT GGCCCCCCTC CAACGA                     46
```

(2) INFORMATION FOR SEQ ID NO: 6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

GGAAGTGACT AAC                                        13

(2) INFORMATION FOR SEQ ID NO: 7:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

GAAAGTGACT TTC                                        13

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

GSTGTGGAAW GT                                         12

(2) INFORMATION FOR SEQ ID NO: 9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

CGTTGCGAAA GT                                         12

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

GGCCACGTGA CC                                         12

(2) INFORMATION FOR SEQ ID NO: 11:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 11:

TGCCACTGTC GA                                                            12

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CGTACAGGGG GGTACGTCAT C                                                  21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

TGTACAGGGG GGTACGTCAT C                                                  21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CGTACAGGGG GGTACGTCAC A                                                  21

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CGTACAGGGG GGTACGTCAC G                                                  21

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 16:

CGTACAGGGG GGTACGTCAC A                                              21

(2) INFORMATION FOR SEQ ID NO: 17:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 17:

CGTACAGGGG GGTACGTCTC A                                              21

(2) INFORMATION FOR SEQ ID NO: 18:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 18:

AAGAGGCGTT CC                                                        12

(2) INFORMATION FOR SEQ ID NO: 19:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 19:

AGGAGGCGTT CC                                                        12

(2) INFORMATION FOR SEQ ID NO: 20:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 20:

AAAAGGCGTT CC                                                        12

(2) INFORMATION FOR SEQ ID NO: 21:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 21:

AAGAGGCGTT AC                                                         12

(2) INFORMATION FOR SEQ ID NO: 22:

(i) SEQUENCE CHARACTERISTICS:
              (A) LENGTH: 187 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 22:

GCAGTAGGTA TACGCAAGGC GGTCCGGGTG GATGCACGGG AACGGCGGAC AACCGGCCGC      60

TGGGGGCAGT GAATCGGCGC TTAGCCGAGA GGGGCAACCT GGGCCCAGCG GAGCCGCGCA     120

GGGGCAAGTA ATTTCAAATG AACGCTCTCC AAGAAGATAC TCCACCCGGA CCATCAACGG     180

TGTTCAG                                                              187

(2) INFORMATION FOR SEQ ID NO: 23:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 23:

GCAGTAGGTA TACGCAAGG                                                  19

(2) INFORMATION FOR SEQ ID NO: 24:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 24:

CAGTGAATCG GCGCTTAGC                                                  19

(2) INFORMATION FOR SEQ ID NO: 25:

(i) SEQUENCE CHARACTERISTICS:
              (A) LENGTH: 19 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 25:

GACCATCAAC GGTGTTCAG                                                  19

(2) INFORMATION FOR SEQ ID NO: 26:

(i) SEQUENCE CHARACTERISTICS:
              (A) LENGTH: 1348 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO: 26:

| | | | | | |
|---|---|---|---|---|---|
| ATGGCAAGAC | GAGCTCGCAG | ACCGAGAGGC | CGATTTTACT | CCTTCAGAAG | AGGACGGTGG | 60 |
| CACCACCTCA | AGCGACTTCG | ACGAAGATAT | AAATTTCGAC | ATCGGAGGAG | ACAGCGGTAT | 120 |
| CGTAGACGAG | CTTTTAGGAA | GGCCTTTCAC | AACCCCCGCC | CCGGTACGTA | TAGTGTGAGG | 180 |
| CTGCCGAACC | CCCAATCTAC | TATGACTATC | CGCTTCCAAG | GGGTCATCTT | TCTCACGGAA | 240 |
| GGACTCATTC | TGCCTAAAAA | CAGCACAGCG | GGGGCTATG | CAGACCACAT | GTACGGGGCG | 300 |
| AGAGTCGCCA | AGATCTCTGT | GAACCTGAAA | GAGTTCCTGC | TAGCCTCAAT | GAACCTGACA | 360 |
| TACGTGAGCA | AAATCGGAGG | CCCCATCGCC | GGTGAGTTGA | TTGCGGACGG | GTCTAAATCA | 420 |
| CAAGCCGCGG | ACAATTGGCC | TAATTGCTGG | CTGCCGCTAG | ATAATAACGT | GCCCTCCGCT | 480 |
| ACACCATCGG | CATGGTGGAG | ATGGGCCTTA | ATGATGATGC | AGCCCACGGA | CTCTTGCCGG | 540 |
| TTCTTTAATC | ACCCAAAGCA | GATGACCCTG | CAAGACATGG | GTCGCATGTT | TGGGGCTGG | 600 |
| CACCTGTTCC | GACACATTGA | AACCCGCTTT | CAGCTCCTTG | CCACTAAGAA | TGAGGGATCC | 660 |
| TTCAGCCCCG | TGGCGAGTCT | TCTCTCCCAG | GGAGAGTACC | TCACGCGTCG | GGACGATGTT | 720 |
| AAGTACAGCA | GCGATCACCA | GAACCGGTGG | CAAAAAGGCG | ACAACCGAT | GACGGGGGGC | 780 |
| ATTGCTTATG | CGACCGGGAA | AATGAGACCC | GACGAGCAAC | AGTACCCTGC | TATGCCCCCA | 840 |
| GACCCCCCGA | TCATCACCGC | TACTACAGCG | CAAGGCACGC | AAGTCCGCTG | CATGAATAGC | 900 |
| ACGCAAGCTT | GGTGGTCATG | GGACACATAT | ATGAGCTTTG | CAACACTCAC | AGCACTCGGT | 960 |
| GCACAATGGT | CTTTTCCTCC | AGGGCAACGT | TCAGTTTCTA | GACGGTCCTT | CAACCACCAC | 1020 |
| AAGGCGAGAG | GAGCCGGGGA | CCCCAAGGGC | CAGAGATGGC | ACACGCTGGT | GCCGCTCGGC | 1080 |
| ACGGAGACCA | TCACCGACAG | CTACATGTCA | GCACCCGCAT | CAGAGCTGGA | CACTAATTTC | 1140 |
| TTTACGCTTT | ACGTAGCGCA | AGGCACAAAT | AAGTCGCAAC | AGTACAAGTT | CGGCACAGCT | 1200 |
| ACATACGCGC | TAAAGGAGCC | GGTAATGAAG | AGCGATGCAT | GGGCAGTGGT | ACGCGTCCAG | 1260 |
| TCGGTCTGGC | AGCTGGGTAA | CAGGCAGAGG | CCATACCCAT | GGGACGTCAA | CTGGGCGAAC | 1320 |
| AGCACCATGT | ACTGGGGGAC | GCAGCCCT | | | | 1348 |

(2) INFORMATION FOR SEQ ID NO: 27:

(i) SEQUENCE CHARACTERISTICS:
  (A) LENGTH: 649 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO: 27:

| | | | | | |
|---|---|---|---|---|---|
| ATGCACGGGA | ACGGCGGACA | ACCGGCCGCT | GGGGGCAGTG | AATCGGCGCT | TAGCCGAGAG | 60 |
| GGCAACCTG | GCCCAGCGG | AGCCGCGCAG | GGCAAGTAA | TTTCAAATGA | ACGCTCTCCA | 120 |
| AGAAGATACT | CCACCCGGAC | CATCAACGGT | GTTCAGGCCA | CCAACAAGTT | CACGGCCGTT | 180 |
| GGAAACCCCT | CACTGCAGAG | AGATCCGGAT | TGGTATCGCT | GGAATTACAA | TCACTCTATC | 240 |
| GCTGTGTGGC | TGCGCGAATG | CTCGCGCTCC | CACGCTAAGA | TCTGCAACTG | CGGACAATTC | 300 |
| AGAAAGCACT | GGTTTCAAGA | ATGTGCCGGA | CTTGAGGACC | GATCAACCCA | GCCTCCCTC | 360 |
| GAAGAAGCGA | TCCTGCGACC | CCTCCGAGTA | CAGGGTAAGC | GAGCTAAAAG | AAAGCTTGAT | 420 |
| TACCACTACT | CCCAGCCGAC | CCCGAACCGC | AAAAAGGCGT | ATAAGACTGT | AAGATGGCAA | 480 |

-continued

```
GACGAGCTCG CAGACCGAGA GGCCGATTTT ACTCCTTCAG AAGAGGACGG TGGCACCACC      540

TCAAGCGACT TCGACGAAGA TATAAATTTC GACATCGGAG GAGACAGCGG TATCGTAGAC      600

GAGCTTTTAG GAAGGCCTTT CACAACCCCC GCCCGGTAC GTATAGTGT                   649

(2) INFORMATION FOR SEQ ID NO: 28:

(i) SEQUENCE CHARACTERISTICS:
        (A) LENGTH: 364 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

ATGAACGCTC TCCAAGAAGA TACTCCACCC GGACCATCAA CGGTGTTCAG GCCACCAACA       60

AGTTCACGGC CGTTGGAAAC CCCTCACTGC AGAGAGATCC GGATTGGTAT CGCTGGAATT      120

ACAATCACTC TATCGCTGTG TGGCTGCGCG AATGCTCGCG CTCCCACGCT AAGATCTGCA      180

ACTGCGGACA ATTCAGAAAG CACTGGTTTC AAGAATGTGC CGGACTTGAG GACCGATCAA      240

CCCAAGCCTC CCTCGAAGAA GCGATCCTGC GACCCCTCCG AGTACAGGGT AAGCGAGCTA      300

AAAGAAAGCT TGATTACCAC TACTCCCAGC CGACCCCGAA CCGCAAAAAG GCGTATAAGA      360

CTGT                                                                   364
```